United States Patent [19]

Gwynne et al.

[11] Patent Number: 5,503,991
[45] Date of Patent: Apr. 2, 1996

[54] VECTORS FOR USE IN FILAMENTOUS FUNGI

[75] Inventors: David I. Gwynne, Brampton; Francis P. Buxton, Toronto; Mark H. Pickett, Brampton; Roger W. Davies, Ontario, all of Canada; Claudio Scazzocchio, Bures sur Yvette, France

[73] Assignee: Gist-Brocades, Delft, Netherlands

[21] Appl. No.: 237,405

[22] Filed: May 2, 1994

Related U.S. Application Data

[63] Continuation of Ser. No. 977,832, Nov. 17, 1992, abandoned, which is a continuation of Ser. No. 811,404, Dec. 20, 1985, Pat. No. 5,198,345.

[30] Foreign Application Priority Data

Apr. 15, 1985 [CA] Canada ................................. 479135

[51] Int. Cl.⁶ ............................. C12N 15/63; C12N 15/80
[52] U.S. Cl. .................. 435/69.1; 435/252.3; 435/254.1; 435/254.11; 435/254.3; 435/256.1; 435/320.1; 435/172.1; 435/172.3; 536/23.1; 536/24.1
[58] Field of Search ........................... 435/69.1, 320.1, 435/172.1, 172.3, 252.3, 254.1, 254.11, 254.3, 256.1; 536/23.1, 24.1

[56] References Cited

U.S. PATENT DOCUMENTS

5,198,345  3/1993  Gwynne et al. ................. 435/69.1

FOREIGN PATENT DOCUMENTS

| | | |
|---|---|---|
| 0099226 | 1/1984 | European Pat. Off. . |
| 0126206 | 11/1984 | European Pat. Off. . |
| 0127304 | 12/1984 | European Pat. Off. . |
| 0136907 | 4/1985 | European Pat. Off. . |
| 0136007 | 4/1985 | European Pat. Off. . |
| 0173378B1 | 3/1986 | European Pat. Off. . |
| 0181213 | 5/1986 | European Pat. Off. . |
| 0215594A2 | 3/1987 | European Pat. Off. . |
| 0225078A2 | 6/1987 | European Pat. Off. . |
| 0238023B1 | 9/1987 | European Pat. Off. . |
| WO84/02921 | 8/1984 | WIPO . |
| WO87/04464 | 7/1987 | WIPO . |

OTHER PUBLICATIONS

E. J. Mullaney et al. "Primary structure of the trpC gene . . . " Mol. Gen. Genet (1985), 199, pp. 37–45.
Talmade, K. et al "Construction of Plasmid Vectors with Unique . . . " Gene, 12 (1980) pp. 235–241.
Svensson, B. et al "Characterization of Two Forms of Glucoamylase . . . ", Carlsberg Res. Commun., vol. 47, pp. 55–69 (1982).
Slocombe, P. et al "High–Level Expression of an Interferon a2 . . . ", Proc. Natl Aca. Sci. USA, vol. 79, pp. 5455–5459, Sep. 1982.
Whittle, D. J. et al "Molecular Cloning of a *Cellumomonas fimi* . . . " Gene, 17 (1982), pp. 139–145.
Ballance, D. J. "Transformation of *Aspergillus nidulans* by the . . . " Chemical Abstracts, vol. 98, 1983, p. 150.
Von Heijne, "Patterns of Amio Acids near Signal–Sequence Cleavage . . . " J. Biochem. 133, 17–21 (1983).
Yleton, M. M. et al "Transformation of *Aspergillus nidulans* by using . . . " Natl Acad. of Sci. USA, vol. 81, Mar. 1984, pp. 1470–1474.
Penttila, M. E. et al "Cloning of *Aspergillus niger* genes in yeast . . . ", Mol Gen Gene (1984) 194:494–499.
Pateman, D. A. et al "Gene for alcohol utilization in the lower . . . " Chemical Abstracts, vol. 100, 1984, p. 108.
Pateman, J. A. "Regulation of Alcohol Dehydrogenase (ADH) and . . . ", 10–Microbial Biochem, vol. 98, 1983, p. 247.
Rothstein, S. J. et al "Secretions of a wheat a–amylase expressed in yeast", 37 Nature 308 (1984) Apr., No. 5960.
Boel, E. et al "Two different types of intervening . . . " Chemical Abstracts, vol. 101 (1984)m p. 158.
Doy, C. H. et al "Genomic clones of *Aspergillus nidulans* containing . . . ", 3–Biochem Genetics, vol. 103, 1985, p. 17753.
Lockington, R. A. et al "Cloning and characterization of the ethanol . . . ", Gene, 33 (1985) pp. 137–149.
Buxton, F. P. et al "Transformation of *Aspergillus niger* using the . . . " Gene, 37 (1985), pp. 207–214.
Van dan Hondel, et al, "Development of a system for analysis . . . ", 3–Biochem. Genetics, vol. 104 (1986) #103399.
Rambosck, J. et al "Recombinant DNA in filamentous fungi progress . . . ", CRC Critical Rev. in Biotech, vol. 6, Issue 4 (1987), pp. 357–393.
Van Gorcom, R. F. M. et al "Expression of an *Escherichia coli* β–galactosidase fusion . . . " Gene 40 (1985), pp. 99–106.
Suggs et al, 1981 PNAS, 78–6613.
Tuito et al, 1982 EMBOJ 1(s). 603.
Tilburn et al, 1983 Gene 26.205.
Mariatis et al, 1982 "Molecular cloning cold spring" Harbor Laboratory.

*Primary Examiner*—Mindy Fleisher
*Assistant Examiner*—David Guzo
*Attorney, Agent, or Firm*—Nixon & Vanderhye

[57] ABSTRACT

Novel vectors are disclosed for use in filamentous fungi such as Aspergillus sp. in particular, whereby protein coding regions may be inserted therein to achieve expression or expression followed by secretion of the coded protein from the host. Signal peptide sequences and promoter sequences valuable for this purpose are disclosed as are expression vectors containing coding regions native or foreign to the fungal host. In accordance with the invention, a filamentous fungus such as Aspergillus may be provided with foreign or natural coding regions associated with foreign or natural promoter sequences and optionally signal peptide sequences which can be used to control the expression and/or secretion of the proteins encoded by these coding regions.

18 Claims, 22 Drawing Sheets

```
-800                    -780                    -760
  .                       .                       .
GGATACAGTTGGGCATTTCTAGGGCTGAATGGGAAGGAGAGAGTTTTGAAATAGGCGTTC
ATTTTCCAGCATGTCGACCAAACTGCAAATACAAGTGTACGAAGGACGGCGTATAGTAAC

-740                    -720                    -700
  .                       .                       .
CGTTCTGCTTAGGGTATTTGGGAACAATCAATGTTCAATGTACATTTAATCCACGATTTT
GGAAGGACTCCGAGCCAAGCAACCGAGAATGACGTCTCAGACTCTGCGAGTGAGGCGGGC

-680                    -660                    -640
  .                       .                       .
ATAAAACGTCATCCTTTGCCCTCCCTTCTTATTTGCCAATACCAAAAATCTTACTCCAGT
TCCAATCAGGGAACTTCTGCATGGTCATCAACCCCGCATGATCTTCTCATCACGCCTCTT

-620                    -600                    -580
  .                       .                       .
GGTTCGGTAATCGCAGAGTTAAATCTGGGCTCGGTGGCAGATCTGCGATCGTCCATAACC
GGTTCGTAATTTTCATTTTTGCATTACGGCCTCGGTTATCATCGCAGCCTCCACCACATA

-560                    -540                    -520
  .                       .                       .
GTTCAGATGTTGATTGGAACTGGGTGGGGTAGACAGCTCCGAAGACCGAGTGAACGTATA
GTCGTCAAGATAGGTCCAGAATCAGTCCGCTCTAGGGGGGTAAATCGTAAATTGCAATTC

-500                    -480                    -460
  .                       .                       .
CCTAAGACACTTTGACACGGCCGGAACACTGTAAGTCCCTTCGTATTTCTCCGCCTGTGT
GCATTACGGTCTGGGTTATCGATCGCGGGGATCCTCAACTTTGTTTCAGAACCAGGGTGC

-440                    -420                    -400
  .                       .                       .
GGAGCTACCATCCAATAACCCCCAGCTGAAAAAGCTGATTGTCGATAGTTGTGATAGTTC
TGTAGGTTGTAGATCGTAAGTTTCATCCTGCATTACCCGCCTCGGTTATTATCGCGAGCT

-380                    -360                    -340
  .                       .                       .
CCACTTGTCCGTCCGCATCGGCATCCGCAGCTCGGGATAGTTCCGACCTAGGATTGGATG
CTTCAACGTGTTTTCAGAATCATCTAGGCTCGTGGAGGCAGTGGGCACCGCGGCGAAGGG

-320                    -300  ╱14              -280
  .                       .                       .
CATGCGGAACCGCACGAGGGCGGGGCGGAAATTGACACACCACTCCTCTCCACGCAgCCG
GACGGAATGCAGTTCACCTGGACTCGGCTCTTGAAGACCAGTGGGGCACTTCGGCGGGTT

-260                    -240                    -220
  .                       .                       .
TTCAAGAGGTACGCGTATAGAGCCGTATAGAGCAGAGACGGAGCACTTTCTGGTACTGTC
GCTAGCTTGCTACATGTAATTTCCATGGGTAACAGCTATCCTCAACAAGAGCGGCTCCGC
```

FIG. 1A

```
                -200                      -180                     -160
                  .                         .                        .
       CGCACGGGATGTCCGCACGGAGAGCCACAAACGAGCGGGGCCCCGTACGTGCTCTCCTAC
       TTGACCTGTTCCCCTCCTTTCCCCTCTTTTGCTGCGACACTGGCTCAGTGCTACAAAGCC

16
        -140                     -120               /  -100
                 .                  .              ******  .
       CCCAGGATCGCATCCTCGCATAGCTGAACATCTATATAAAGACCCCCAAGGTTCTCAGTC
       AGAGCGGTATTATTAAAGCTCCCTCGTCCTCCCACCGAGCCAGCATTTCTCCCTACTCCA
                    ********                                           #
         -80        /  16'         -60                      -40
                                 .*#      #.
       TCACCAACATCATCAACCAACAATCAACAGTTCTCTACTCAGTTAATTAGAACACTTCCA
       ACTCTCCTCTCCCAAGATACCCATATTTCCCGCTCACCATGTCTGATTTGTTCACCACCA
       #
                                          12
          -20                      0      /                20         22
                .                    .                       .        /
       ATCCTATCACCTCGCCTCAAAATGTGCATCCCCACTATGCAATGGGCCCAGGTCGCCGAG
                                       MetCysIleProThrMetGlnTrpAlaGlnValAlaGlu
       TCGAGACTCCGGTCATCAAATATGAGCAGCTCTCGGCTGTATGACGTTTTCTCGCCTCCT
                                    /MetSerSerSerArgGluTyrAspValPheSerProPro
                                  12'

40                       60                       80
                 .                     .                       .
       AAGGTCGGCGGCCCGCTCGTCTACAAGCAGATCCCCGTCCCTAAGCCCGGTCCCGACCAG
       LysValGlyGlyProLeuValTyrLysGlnIleProValProLysProGlyProAspGln
       GATTTTTTTTGTGTTGTGTTTATTAACGATCATTCGGGTTGTAGGTTCATCAACAACGAG
       AspPhePheCysValValPheIleAsnAspHisSerGlyCysArgPheIleAsnAsnGlu 100                      120                      140
                 .                     .                       .
       ATCCTTGTGAAGATCCGCTACTCTGGGGTTTGCCACACCGACCTACACGCTATGATGGGT
       IleLeuValLysIleArgTyrSerGlyValCysHisThrAspLeuHisAlaMetMetGly
       TTCGTGAAGGCCGTTGAGGGCAAGACCTTCCAGGTCATCAACCCCTCCAACCGAGAAGGT      }10
       PheValLysAlaValGluGlyLysThrPheGlnValIleAsnProSerAsnArgGluGly 160                      180                      200
                 .                     .                       .
        CACTGGCCAATCCCCGTCAAAATGCCGCTCGTCGGTGGGCACGAAGGAGCAGGAATCGTC
        HisTrpProIleProValLysMetProLeuValGlyGlyHisGluGlyAlaGlyIleVal
        CAACCGAGGAAGGATGTTGATGTCGCCGTCGCTGCTGCCCGTGCTGCCTTTGAGGGGCCA
        GlnProArgLysAspValAspValAlaValAlaAlaArgAlaAlaPheGluGlyPro 220                      240
                 .                     .
        GTGGCAAAGGGCGAACTGGTCCACGAATTC
        ValAlaLysGlyGluLeuValHisGluPhe
        TGGCGCCAGGTCACCCCCTCTGAGCGTGGC
        TrpArgGlnValThrProSerGluArgGly
```

FIG. 1B

```
    CGCGCAGATCTCGATATCGAGCT
1   -----------------------  23
       GTCTAGAGCTATAGC
```

ArgAlaAspLeuAspIleGlu??

FIG. 5A

```
    CGCGCAAGATCTCGATATCGAGCT
1   ------------------------  24
       GTTCTAGAGCTATAGC
```

ArgAlaArgSerArgTyrArgAla

FIG. 5B

```
    CGCGCAAAGATCTCGATATCGAGCT
1   -------------------------  25
       GTTTCTAGAGCTATAGC
```

ArgAlaLysIleSerIleSerSer?

FIG. 5C

```
    GAATTCAAGCTAGATGCTAAGCGATATTGCATGGCAATATGTGTTGATGCATGTGCTTCT
1   ------------+----------+----------+----------+----------+----------+   60
    CTTAAGTTCGATCTACGATTCGCTATAACGTACCGTTATACACAACTACGTACACGAAGA
```

```
                                        ⌐97   ⌐102
    ⁻CCTTCAGCTTCCCCTCGTGCAGATGAAGGTTTGGCTATAAATTGAAGTGGTTGGTCGGG
61  ------------+----------+----------+----------+----------+----------+   120
    AGGAAGTCGAAGGGGAGCACGTCTACTTCCAAACCGATATTTAACTTCACCAACCAGCCC
```

```
    GTTCCGTGAGGGGCTGAAGTGCTTCCTCCCTTTTAGACGCAACTGAGAGCCTGAGCTTCA
121 ------------+----------+----------+----------+----------+----------+   180
    CAAGGCACTCCCCGACTTCACGAAGGAGGGAAAATCTGCGTTGACTCTCGGACTCGAAGT
```

```
                              ⌐206
    TCCCCAGCATCATTACACCTCAGCAATGTCGTTCCGATCTCTACTCGCCCTGAGCGGCCT
181 ------------+----------+----------+----------+----------+----------+   240
    AGGGGTCGTAGTAATGTGGAGTCGTTACAGCAAGGCTAGAGATGAGCGGGACTCGCCGGA
                              MetSerPheArgSerLeuLeuAlaLeuSerGlyLe
```

```
    CGTCTGCACAGGGTTGGCAAATGTGATTTCCAAGCGCGC
241 ------------+----------+----------+---------+   280
    GCAGACGTGTCCCAACCGTTTACACTAAAGGTTCGCGCG
    uValCysThrGlyLeuAlaAsnValIleSerLysArgAla
```

FIG. 6

```
                promoter                          signal sequence
      ┌─────────────────────────┐┌──────────────────────────────────────────────┐
      TCCCCAGCATCATTACACCTCAGCAATGTCGTTCCGATCTCTACTCGCCCTGAGCGGCCT
181   ─────────+─────────+─────────+─────────+─────────+─────────+  240
      AGGGGTCGTAGTAATGTGGAGTCGTTACAGCAAGGCTAGAGATGAGCGGGACTCGCCGGA
                                 MetSerPheArgSerLeuLeuAlaLeuSerGlyLeu
```

```
                                            ┌─linker B'
                                            │      Dde (filed site)
                              32┐  ┌─34  36─┐  │
      CGTCTGCACAGGGTTGGCAAATGTGATTTCCAAGCGCGCAAGATCTCGATTCAGCTGCAA
241   ─────────+─────────+─────────+─────────+─────────+─────────+  300
      GCAGACGTGTCCCAACCGTTTACACTAAAGGTTCGCGCGTTCTAGAGCTAAGTCGACGTT
      ValCysThrGlyLeuAlaAsnValIleSerLysArgAlaArgSerArgPheSerCysLys
```

```
                          interferon structural gene
      ┌────────────────────────────────────────────────────────────┐
      GTCAAGCTGCTCTGTGGGCTGTGATCTGCCTCAAACCCACAGCCTGGGTAGCAGGAGGAC
301   ─────────+─────────+─────────+─────────+─────────+─────────+  360
      CAGTTCGACGAGACACCCGACACTAGACGGAGTTTGGGTGTCGGACCCATCGTCCTCCTG SerSerCysSerValGlyCysAspLeuProGlnThrHisSerLeuGlySerArgArgThr
```

```
      CTTGATGCTC                                          TATTTGGT
361   ─────────+  .  .  .  .  .  .  .  .  .  .  .        ────────
      GAACTACGAG                                          ATAAACCA
                                              ┌─40 ┌─38 ┌─linker B"
      AAAAAAAAAAAAAAAAAAAAAAAAAAAAAAAAAAAAAAAAAACCGGATCATCGAGCTC
     ─+─────────+─────────+─────────+─────────+─────────+─────────+  1200
      TTTTTTTTTTTTTTTTTTTTTTTTTTTTTTTTTTTTTTTTTTGGCCTAGTAGCTCGAG
```

FIG. 8

PROMOTER

```
        GGATACAGTTGGGCATTTCTAGGGCTGAA
        ---------+---------+---------+  1200
        CCTATGTCAACCCGTAAAGATCCCGACTT
```

```
      TGGGAAGGAGAGAGTTTTGAAATAGGCGTTCCGTTCTGCTTAGGGTATTTGGGAACAATC
1201  ---------+---------+---------+---------+---------+---------+  1260
      ACCCTTCCTCTCTCAAAACTTTATCCGCAAGGCAAGACGAATCCCATAAACCCTTGTTAG
```

```
      AATGTTCAATGTACATTTAATCCACGATTTTATAAAACGTCATCCTTTGCCCTCCCTTCT
1261  ---------+---------+---------+---------+---------+---------+  1320
      TTACAAGTTACATGTAAATTAGGTGCTAAAATATTTTGCAGTAGGAAACGGGAGGGAAGA
```

```
      TATTTGCCAATACCAAAAATCTTACTCCAGTGGTTCGGTAATCGCAGAGTTAAATCTGGG
1321  ---------+---------+---------+---------+---------+---------+  1380
      ATAAACGGTTATGGTTTTTAGAATGAGGTCACCAAGCCATTAGCGTCTCAATTTAGACCC
```

```
      CTCGGTGGCAGATCTGCGATCGTCCATAACCGTTCAGATGTTGATTGGAACTGGGTGGGG
1381  ---------+---------+---------+---------+---------+---------+  1440
      GAGCCACCGTCTAGACGCTAGCAGGTATTGGCAAGTCTACAACTAACCTTGACCCACCCC
```

```
      TAGACAGCTCCGAAGACCGAGTGAACGTATACCTAAGACACTTTGACACGGCCGGAACAC
1441  ---------+---------+---------+---------+---------+---------+  1500
      ATCTGTCGAGGCTTCTGGCTCACTTGCATATGGATTCTGTGAAACTGTGCCGGCCTTGTG
```

```
      TGTAAGTCCCTTCGTATTTCTCCGCCTGTGTGGAGCTACCATCCAATAACCCCCAGCTGA
1501  ---------+---------+---------+---------+---------+---------+  1560
```

FIG. 11A

```
                ACATTCAGGGAAGCATAAAGAGGCGGACACACCTCGATGGTAGGTTATTGGGGGTCGACT

AAAAGCTGATTGTCGATAGTTGTGATAGTTCCCACTTGTCCGTCCGCATCGGCATCCGCA
1561   ----------+---------+---------+---------+---------+---------+ 1620
       TTTTCGACTAACAGCTATCAACACTATCAAGGGTGAACAGGCAGGCGTAGCCGTAGGCGT

GCTCGGGATAGTTCCGACCTAGGATTGGATGCATGCGGAACCGCACgAGGGCGGGGCGGA
1621   ----------+---------+---------+---------+---------+---------+ 1680
       CGAGCCCTATCAAGGCTGGATCCTAACCTACGTACGCCTTGGCGTGcTCCCGCCCCGCCT

AATTGACACACCACTCCTCTCCACGCAgCCGTTCAAGAGGTACGCGTATAGAGCCGTATA
1681   ----------+---------+---------+---------+---------+---------+ 1740
       TTAACTGTGTGGTGAGGAGAGGTGCGTcGGCAAGTTCTCCATGCGCATATCTCGGCATAT

GAGCAGAGACGGAGCACTTTCTGGTACTGTCCGCACGGGATGTCCGCACGGAGAGCCACA
1741   ----------+---------+---------+---------+---------+---------+ 1800
       CTCGTCTCTGCCTCGTGAAAGACCATGACAGGCGTGCCCTACAGGCGTGCCTCTCGGTGT

AACGAGCGGGGCCCCGTACGTGCTCTCCTACCCCAGGATCGCATCCTCGCATAGCTGAAC
1801   ----------+---------+---------+---------+---------+---------+ 1860
       TTGCTCGCCCCGGCGCATGCACGAGAGGATGGGGTCCTAGCGTAGGAGCGTATCGACTTG

ATCTATATAAAGACCCCCAAGGTTCTCAGTCTCACCAACATCATCAACCAACAATCAACA
1861   ----------+---------+---------+---------+---------+---------+ 1920
```

FIG. 11B

TAGATATATTTCTGGGGGTTCCAAGAGTCAGAGTGGTTGTAGTAGTTGGTTGTTAGTTGT

Sal I → SYNTHETIC SIGNAL SEQUENCE

```
       GGGTCGACATGTACCGGTTCCTCGCCGTCATCTCGGCCTTCCTCGCCACTGCCTTCGCCA
1921   ----------+---------+---------+---------+---------+---------+ 1980
       CCCAGCTGTACATGGCCAAGGAGCGGCAGTAGAGCCGGAAGGAGCGGTGACGGAAGCGGT

MetTyrArgPheLeuAlaValIleSerAlaPheLeuAlaThrAlaPheAlaLys
```

XbaI  BamHI/BglII FUSION → IFα2 CODING REGION

```
       AGTCTAGAGGATCTCGATTCAGCTGCAAGTCAAGCTGCTCTGTGGGCTGTGATCTGCCTC
1981   ----------+---------+---------+---------+---------+---------+ 2040
       TCAGATCTCCTAGAGCTAAGTCGACGTTCAGTTCGACGAGACACCCGACACTAGACGGAG

SerArgGlySerArgPheSerCysLysSerSerCysSerValGlyCysAspLeuProGln
```

```
       AAACCCACAGCCTGGGTAGCAGGAGGACCTTGATGCTCCTGGCACAGATGAGGAGAATCT
2041   ----------+---------+---------+---------+---------+---------+ 2100
       TTTGGGTGTCGGACCCATCGTCCTCCTGGAACTACGAGGACCGTGTCTACTCCTCTTAGA

ThrHisSerLeuGlySerArgArgThrLeuMetLeuLeuAlaGlnMetArgArgIleSer
```

```
       CTCTTTTCTCCTGCTTGAAGGACAGACATGACTTTGGATTTCCCCAGGAGGAGTTTGGCA
2101   ----------+---------+---------+---------+---------+---------+ 2160
       GAGAAAAGAGGACGAACTTCCTGTCTGTACTGAAACCTAAAGGGGTCCTCCTCAAACCGT

LeuPheSerCysLeuLysAspArgHisAspPheGlyPheProGlnGluGluPheGlyAsn
```

```
       ACCAGTTCCAAAAGGCTGAAACCATCCCTGTCCTCCATGAGATGATCCAGCAGATCTTCA
2161   ----------+---------+---------+---------+---------+---------+ 2220
       TGGTCAAGGTTTTCCGACTTTGGTAGGGACAGGAGGTACTCTACTAGGTCGTCTAGAAGT

GlnPheGlnLysAlaGluThrIleProValLeuHisGluMetIleGlnGlnIlePheAsn
```

```
     ATCTCTTCAGCACAAAGGACTCATCTGCTGCTTGGGATGAGACCCTCCTAGACAAATTCT
2221 ------------+---------+---------+---------+---------+---------+ 2280
     TAGAGAAGTCGTGTTTCCTGAGTAGACGACGAACCCTACTCTGGGAGGATCTGTTTAAGA

LeuPheSerThrLysAspSerSerAlaAlaTrpAspGluThrLeuLeuAspLysPheTyr
```

```
     ACACTGAACTCTACCAGCAGCTGAATGACCTGGAAGCCTGTGTGATACAGGGGGTGGGGG
2281 ------------+---------+---------+---------+---------+---------+ 2340
     TGTGACTTGAGATGGTCGTCGACTTACTGGACCTTCGGACACACTATGTCCCCCACCCCC

ThrGluLeuTyrGlnGlnLeuAsnAspLeuGluAlaCysValIleGlnGlyValGlyVal
```

```
     TGACAGAGACTCCCCTGATGAAGGAGGACTCCATTCTGGCTGTGAGGAAATACTTCCAAA
2341 ------------+---------+---------+---------+---------+---------+ 2400
     ACTGTCTCTGAGGGGACTACTTCCTCCTGAGGTAAGACCGACACTCCTTTATGAAGGTTT

ThrGluThrProLeuMetLysGluAspSerIleLeuAlaValArgLysTyrPheGlnArg
```

```
     GAATCACTCTCTATCTGAAAGAGAAGAAATACAGCCCTTGTGCCTGGGAGGTTGTCAGAG
2401 ------------+---------+---------+---------+---------+---------+ 2460
     CTTAGTGAGAGATAGACTTTCTCTTCTTTATGTCGGGAACACGGACCCTCCAACAGTCTC

IleThrLeuTyrLeuLysGluLysLysTyrSerProCysAlaTrpGluValValArgAla
```

```
     CAGAAATCATGAGATCTTTTTCTTTGTCAACAAACTTGCAAGAAAGTTTAAGAAGTAAGG
2461 ------------+---------+---------+---------+---------+---------+ 2520
     GTCTTTAGTACTCTAGAAAAAGAAACAGTTGTTTGAACGTTCTTTCAAATTCTTCATTCC

GluIleMetArgSerPheSerLeuSerThrAsnLeuGlnGluSerLeuArgSerLysGlu
```

FIG. 11D

```
            STOP
            ↙
       AATGAAAACTGGTTCAACATGGAAATGATTTTCATTGATTCGTATGCCAGCTCACCTTTT
2521   ----------+---------+---------+---------+---------+---------+  2580
       TTACTTTTGACCAAGTTGTACCTTTACTAAAAGTAACTAAGCATACGGTCGAGTGGAAAA

TATGATCTGCCATTTCAAAGACTCATGTTTCTGCTATGACCATGACACGATTTAAATCTT
2581   ----------+---------+---------+---------+---------+---------+  2640
       ATACTAGACGGTAAAGTTTCTGAGTACAAAGACGATACTGGTACTGTGCTAAATTTAGAA

TTCAAATGTTTTTAGGAGTATTAATCAACATTGTATTCAGCTCTTAAGGCACTAGTCCCT
2641   ----------+---------+---------+---------+---------+---------+  2700
       AAGTTTACAAAAATCCTCATAATTAGTTGTAACATAAGTCGAGAATTCCGTGATCAGGGA

TACAGAGGACCATGCTGACTGATCCATTATCTATTTAAATATTTTTAAAATATTATTTAT
2701   ----------+---------+---------+---------+---------+---------+  2760
       ATGTCTCCTGGTACGACTGACTAGCTAATAGATAAATTTATAAAAATTTTATAATAAATA

TTAACTATTTATAAAACAACTTATTTTTGTTCATATTATGTCATGTGCACCTTTGCACAG
2761   ----------+---------+---------+---------+---------+---------+  2820
       AATTGATAAATATTTTGTTGAATAAAAACAAGTATAATACAGTACACGTGGAAACGTGTC

TGGTTAATGTAATAAAATATGTTCTTTGTATTTGGTAAAAAAAAAAAAAAAAAAAAAAAA
2821   ----------+---------+---------+---------+---------+---------+  2880
       ACCAATTACATTATTTTATACAAGAAACATAAACCATTTTTTTTTTTTTTTTTTTTTTTT
                                                    EcoRI
                                                     ↓
       AAAAAAAAAAAACCGGATCATCGAGCTCGAATTC
2881   ----------+---------+---------+----   2914
       TTTTTTTTTTTTGGCCTAGTAGCTCGAGCTTAAG
```

FIG. 11E

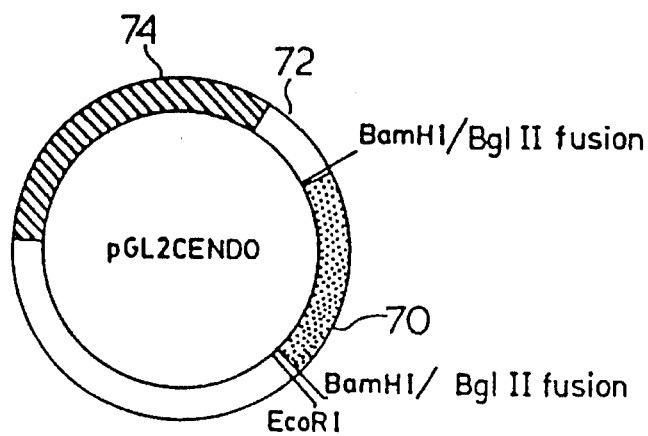
FIG. 12
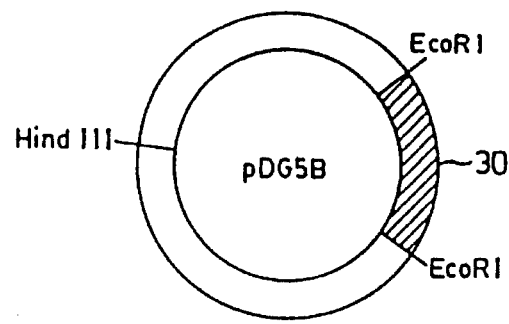
FIG. 14
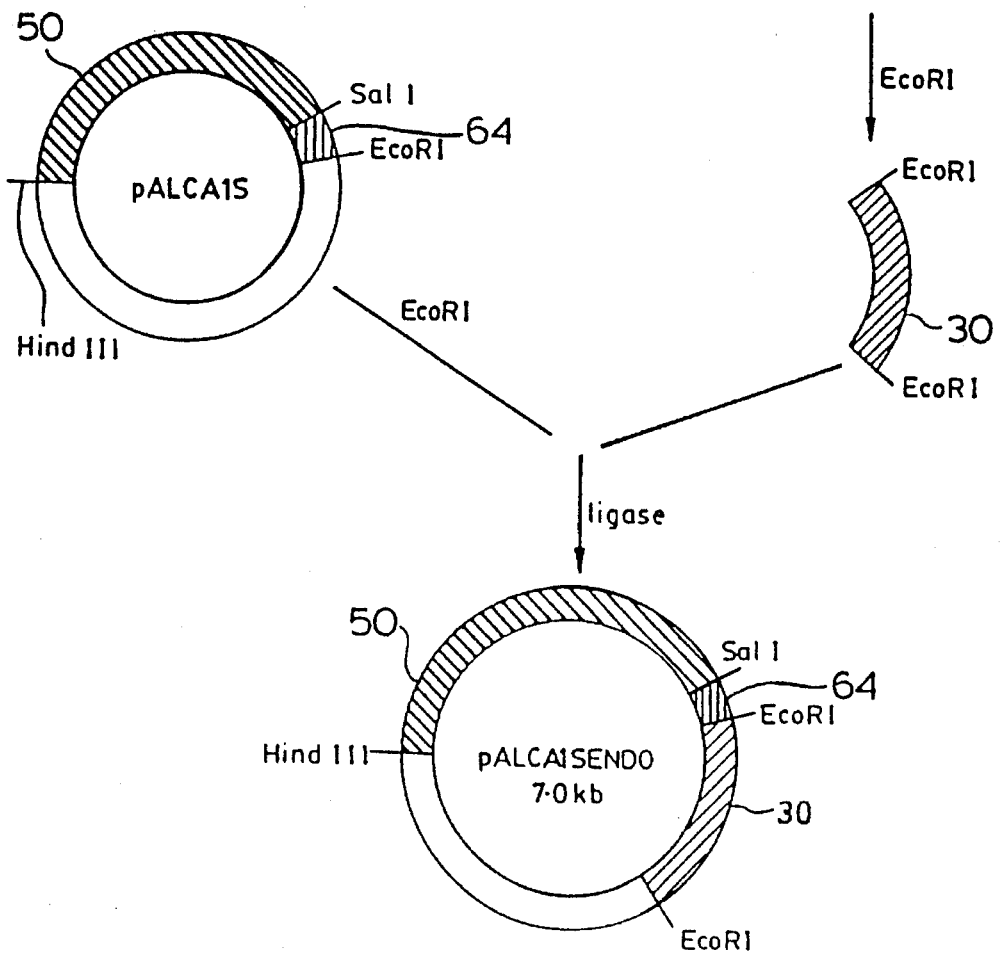

```
                 ┌─EcoRI
                ┌─┴─┐
     GAATTCAAGCTAGATGCTAAGCGATATTGCATGGCAATATGTGTTGATGCATGTGCTTCT
  1  ──────────+──────────+──────────+──────────+──────────+──────────+  60
     CTTAAGTTCGATCTACGATTCGCTATAACGTACCGTTATACACAACTACGTACACGAAGA

TCCTTCAGCTTCCCCTCGTGCAGATGAAGGTTTGGCTATAAATTGAAGTGGTTGGTCGGG
 61  ──────────+──────────+──────────+──────────+──────────+──────────+  120
     AGGAAGTCGAAGGGGAGCACGTCTACTTCCAAACCGATATTTAACTTCACCAACCAGCCC

GTTCCGTGAGGGGCTGAAGTGCTTCCTCCCTTTTAGACGCAACTGAGAGCCTGAGCTTCA
121  ──────────+──────────+──────────+──────────+──────────+──────────+  180
     CAAGGCACTCCCCGACTTCACGAAGGAGGGAAAATCTGCGTTGACTCTCGGACTCGAAGT
                                               glucoamylase signal sequence
                                              ┌─────────────────────────
     TCCCCAGCATCATTACACCTCAGCAATGTCGTTCCGATCTCTACTCGCCCTGAGCGGCCT
181  ──────────+──────────+──────────+──────────+──────────+──────────+  240
     AGGGGTCGTAGTAATGTGGAGTCGTTACAGCAAGGCTAGAGATGAGCGGGACTCGCCGGA MetSerPheArgSerLeuLeuAlaLeuSerGlyLeu ┌─BamHI/BglIIfusion
                                                   ┌─┴─┐
                  ┌─72                              ┌─70  ┌─EcoRI
      ...────────┘                                ┘ ┌─┴┐  ┌─┴─┐
     CGTCTGCACAGGGTTGGCAAATGTGATTTCCAAGCGCGCAAAGATCCAG···GAATTC
241  ──────────+──────────+──────────+──────────+──────────+──────────+
     GCAGACGTGTCCCAACCGTTTACACTAAAGGTTCGCGCGTTTCTAGGTC···CTTAAG ValCysThrGlyLeuAlaAsnVal I leSerLysArgAlaLys I leGln
```

FIG. 13

```
                                            Promoter
                                    ─────────────────────────▶
                              GGATACAGTTGGGCATTTCTAGGGCTGAA
                              --------+---------+---------+   1200
                              CCTATGTCAACCCGTAAAGATCCCGACTT TGGGAAGGAGAGAGTTTTGAAATAGGCGTTCCGTTCTGCTTAGGGTATTTGGGAACAATC
1201   --------+---------+---------+---------+---------+---------+   1260
       ACCCTTCCTCTCTCAAAACTTTATCCGCAAGGCAAGACGAATCCCATAAACCCTTGTTAG AATGTTCAATGTACATTTAATCCACGATTTTATAAAACGTCATCCTTTGCCCTCCCTTCT
1261   --------+---------+---------+---------+---------+---------+   1320
       TTACAAGTTACATGTAAATTAGGTGCTAAAATATTTTGCAGTAGGAAACGGGAGGGAAGA TATTTGCCAATACCAAAAATCTTACTCCAGTGGTTCGGTAATCGCAGAGTTAAATCTGGG
1321   --------+---------+---------+---------+---------+---------+   1380
       ATAAACGGTTATGGTTTTTAGAATGAGGTCACCAAGCCATTAGCGTCTCAATTTAGACCC
```

FIG. 15A

```
1381  CTCGGTGGCAGATCTGCGATCGTCCATAACCGTTCAGATGTTGATTGGAACTGGGTGGGG
      ----------+----------+----------+----------+----------+----------+  1440
      GAGCCACCGTCTAGACGCTAGCAGGTATTGGCAAGTCTACAACTAACCTTGACCCACCCC

1441  TAGACAGCTCCGAAGACCGAGTGAACGTATACCTAAGACACTTTGACACGGCCGGAACAC
      ----------+----------+----------+----------+----------+----------+  1502
      ATCTGTCGAGGCTTCTGGCTCACTTGCATATGGATTCTGTGAAACTGTGCCGGCCTTGTG

1501  TGTAAGTCCCTTCGTATTTCTCCGCCTGTGTGGAGCTACCATCCAATAACCCCCAGCTGA
      ----------+----------+----------+----------+----------+----------+  1560
      ACATTCAGGGAAGCATAAAGAGGCGGACACACCTCGATGGTAGGTTATTGGGGGTCGACT

1561  AAAAGCTGATTGTCGATAGTTGTGATAGTTCCCACTTGTCCGTCCGCATCGGCATCCGCA
      ----------+----------+----------+----------+----------+----------+  1620
      TTTTCGACTAACAGCTATCAACACTATCAAGGGTGAACAGGCAGGCGTAGCCGTAGGCGT

1621  GCTCGGGATAGTTCCGACCTAGGATTGGATGCATGCGGAACCGCACgAGGGCGGGGCGGA
      ----------+----------+----------+----------+----------+----------+  1680
      CGAGCCCTATCAAGGCTGGATCCTAACCTACGTACGCCTTGGCGTGcTCCCGCCCCGCCT

1681  AATTGACACACCACTCCTCTCCACGCAgCCGTTCAAGAGGTACGCGTATAGAGCCGTATA
      ----------+----------+----------+----------+----------+----------+  1740
      TTAACTGTGTGGTGAGGAGAGGTGCGTcGGCAAGTTCTCCATGCGCATATCTCGGCATAT
```

FIG. 15B

```
1741  GAGCAGAGACGGAGCACTTTCTGGTACTGTCCGCACGGGATGTCCGCACGGAGAGCCACA  1800
      ----------+----------+----------+----------+----------+----------+
      CTCGTCTCTGCCTCGTGAAAGACCATGACAGGCGTGCCCTACAGGCGTGCCTCTCGGTGT

1801  AACGAGCGGGGCCCCGTACGTGCTCTCCTACCCCAGGATCGCATCCTCGCATAGCTGAAC  1860
      ----------+----------+----------+----------+----------+----------+
      TTGCTCGCCCCGGGGCATGCACGAGAGGATGGGGTCCTAGCGTAGGAGCGTATCGACTTG

1861  ATCTATATAAAGACCCCCAAGGTTCTCAGTCTCACCAACATCATCAACCAACAATCAACA  1920
      ----------+----------+----------+----------+----------+----------+
      TAGATATATTTCTGGGGGTTCCAAGAGTCAGAGTGGTTGTAGTAGTTGGTTGTTAGTTGT

1921  GGGTCGACATGTACCGGTTCCTCGCCGTCATCTCGGCCTTCCTCGCCACTGCCTTCGCCA  1980
      ----------+----------+----------+----------+----------+----------+
      CCCAGCTGTACATGGCCAAGGAGCGGCAGTAGAGCCGGAAGGAGCGGTGACGGAAGCGGT
          MetTyrArgPheLeuAlaValIleSerAlaPheLeuAlaThrAlaPheAlaLys

XBS1         EcoRI
      AGTCTAGAGGATCCCCGGGCGAGCTCGAATTCCCGGGGATCCAG
1981  ----------+----------+----------+----------+----  . . . . . . . .
      TCAGATCTCCTAGGGGCCCGCTCGAGCTTAAGGGCCCCTAGGTC

SerArgGlySerProGlyGluLeuGluPheProGlyIleGln→endoglucanase codins→

┌EcoRI
                           CCCGGGCGAGCTCGAATTC
      . . . . . . . . .   +----------+----------
                           GGGCCCGCTCGAGCTTAAC
```

FIG. 15C

```
    1  CTCCGCCTGTGTGGAGCTACCATCCAATAACCCCCAGCTGAAAAAGCTGATTGTCGATAG
       ----------+----------+----------+----------+----------+----------+  60
       GAGGCGGACACACCTCGATGGTAGGTTATTGGGGGTCGACTTTTTCGACTAACAGCTATC

61  TTGTGATAGTTCCCACTTGTCCGTCCGCATCGGCATCCGCAGCTCGGGATAGTTCCGACC
       ----------+----------+----------+----------+----------+----------+  120
       AACACTATCAAGGGTGAACAGGCAGGCGTAGCCGTAGGCGTCGAGCCCTATCAAGGCTGG

21  TAGGATTGGATGCATGCGGAACCGCACGAGGGCGGGGCGGAAATTGACACACCACTCCTC
       ----------+----------+----------+----------+----------+----------+  80
       ATCCTAACCTACGTACGCCTTGGCGTGCTCCCGCCCCGCCTTTAACTGTGTGGTGAGGAG

181  TCCACGCAGCCGTTCAAGAGGTACGCGTATAGAGCCGTATAGAGCAGAGACGGAGCACTT
       ----------+----------+----------+----------+----------+----------+  240
       AGGTGCGTCGGCAAGTTCTCCATGCGCATATCTCGGCATATCTCGTCTCTGCCTCGTGAA

241  TCTGGTACTGTCCGCACGGGATGTCCGCACGGAGAGCCACAAACGAGCGGGGCCCCGTAC
       ----------+----------+----------+----------+----------+----------+  300
       AGACCATGACAGGCGTGCCCTACAGGCGTGCCTCTCGGTGTTTGCTCGCCCCGGGGCATG

****
  301  GTGCTCTCCTACCCCAGGATCGCATCCTCGCATAGCTGAACATCTATATAAAGACCCCCA
       ----------+----------+----------+----------+----------+----------+  360
       CACGAGAGGATGGGGTCCTAGCGTAGGAGCGTATCGACTTGTAGATATATTTCTGGGGGT
```

FIG. 17A

```
            AGGTTCTCAGTCTCACCAACATCATCAACCAACAATCAACAGGGTCGACTCTAGAGGATC
    361     ---------+---------+---------+---------+---------+---------+   420
            TCCAAGAGTCAGAGTGGTTGTAGTAGTTGGTTGTTAGTTGTCCCAGCTGAGATCTCCTAG
```

```
                    ┌─EcoRI
                    │
            CCCGGGCGAGCTCGAATTCCCCCGGATCCGTCGACCTGCAGGGCGGGGGGGGGTCTTCTCC
    421     ---------+---------+---------+---------+---------+---------+   480
            GGGCCCGCTCGAGCTTAAGGGGGCCTAGGCAGCTGGACGTCCCCCCCCCCCCCAGAAGAGG
                    +----------pUC 7---------+-GC tail ----+-αamylase-
```

```
            ACCGTCCTCTTGCAGAGCACACACAGAGCTGAAGACGATGGCGAACAAACATCTGTCCCT
    481     ---------+---------+---------+---------+---------+---------+   540
            TGGCAGGAGAACGTCTCGTGTGTGTCTCGACTTCTGCTACCGCTTGTTTGTAGACAGGGA
            ---leader--------------------------+MetAlaAsnLysHisLeuSerLeu
                                               +-αamylase signal--------
```

```
            CTCGCTCTTCCTCGTCCTCCTTGGCCTGTCGGCATCTCTAGCTTCCGGCCAA
    541     ---------+---------+---------+---------+---------+--   592
            GAGCGAGAAGGAGCAGGAGGAACCGGACAGCCGTAGAGATCGAAGGCCGGTT
            SerLeuPheLeuValLeuLeuGlyLeuSerAlaSerLeuAlaSerGlyGln
            -----------------------------------------------+nature protein
```

```
            ┌─EcoRI
            │
            -----GAATTC
            -----CTTAAG
```

FIG. 17B 5,503,991

VECTORS FOR USE IN FILAMENTOUS FUNGI

This is a Rule 62 continuation of of application Ser. No. 07/977,832, filed Nov. 17, 1992, now abandoned, which is a Rule 60 continuation of 06/811,404, filed Dec. 20, 1985, now U.S. Pat. No. 5,198,345 issued Mar. 30, 1993.

FIELD OF THE INVENTION

This invention relates to expression and expression followed by secretion of proteins from filamentous fungi.

BACKGROUND OF THE INVENTION

One goal of recombinant DNA technology is the insertion of structural genes which encode commercially or scientifically valuable proteins into a host cell which is readily and economically available. Genes selected for insertion are normally those which encode proteins produced in only limited amounts by their natural hosts or those which are indigenous to hosts too costly to maintain. Transfer of the genetic information in a controlled manner to a host which is capable of producing the protein in either greater yield or more economically in a similar yield provides a more desirable vehicle for protein production.

Genes encoding proteins contain promoter regions of DNA which are essentially attached to the 5' terminus of the protein coding region. The promoter regions contain the binding site for RNA polymerase II. RNA polymerase II effectively catalyses the assembly of the messenger RNA complementary to the appropriate DNA strand of the coding region. In most promoter regions, a nucleotide base sequence related to the sequence TATATA, known generally as a "TATA box" is present and is generally disposed some distance upstream from the start of the coding region and is required for accurate initiation of transcription. Other features important or essential to the proper functioning and control of the coding region are also contained in the promoter region, upstream of the start of the coding region.

Filamentous fungi, particularly the filamentous ascomycetes such as Aspergillus, e.g. *Aspergillus niger*, represent a class of micro-organisms suitable as recipients of foreign genes coding for valuable proteins. *Aspergillus niger* and related species are currently used widely in the industrial production of enzymes e.g. for use in the food industry. Their use is based on the secretory capacity of the micro-organism. Because they are well characterized and because of their wide use and acceptance, there is both industrial and scientific incentive to provide genetically modified and enhanced cells of *A. niger* and related species including *A. nidulans*, in order to obtain useful proteins.

Expression and secretion of foreign proteins from filamentous fungi has not yet been achieved. It is by no means clear that the strategies which have been successful in yeast would be successful in filamentous fungi such as Aspergillus. Evidence has shown that yeast is an unsuitable system for the expression of filamentous fungal genes (Pentilla et al Molec. Gen. Genet. (1984) 194:494–499) and that yeast genes do not express in filamentous fungi (F. Buxton personal communication). Genetic engineering techniques have only recently been developed for *Aspergillus nidulans* and *Aspergillus niger*. These techniques involve the incorporation of exogenously added genes into the Aspergillus genome in a form in which they are able to be expressed.

To date no foreign proteins have been expressed in and secreted from filamentous fungi using these techniques. This has been due to a lack of suitable expression vectors and their constituent components. These components include Aspergillus promoter sequences described above, the region encoding the desired product and the associated sequences which may be added to direct the desired product to the extracellular medium.

As noted, expression of the foreign gene by the host cell requires the presence of a promoter region situated upstream of the region coding for the protein. This promoter region is active in controlling transcription of the coding region with which it is associated, into messenger RNA which is ultimately translated into the desired protein product. Proteins so produced may be categorized into two classes on the basis of their destiny with respect to the host.

A first class of proteins is retained intracellularly. Extraction of the desired protein, when intracellular, requires that the genetically engineered host be broken open or lysed in order to free the product for eventual purification. Intracellular production has several advantages. The protein product can be concentrated i.e. pelleted with the cellular mass, and if the product is labile under extracellular conditions or structurally unable to be secreted, this is a desired method of production and purification.

A second class of proteins are those which are secreted from the cell. In this case, purification is effected on the extracellular medium rather than on the cell itself. The product can be extracted using methods such as affinity chromatography and continuous flow fermentation is possible. Also, certain products are more stable extracellularly and are benefited by extracellular purification. Experimental evidence has shown that secretion of proteins in eukaryotes is almost always dictated by a secretion signal peptide (hereafter called signal peptide) which is usually located at the amino terminus of the protein. Signal peptides have characteristic distributions as described by G. Von Heijne in *Eur. J. Biochem* 17–21 (1983) and are recognizable by those skilled in the art. The signal peptide, when recognized by the cell, directs the protein into the cell's secretory pathway. During secretion, the signal peptide is cleaved off making the protein available for harvesting in its mature form from the extracellular medium.

Both classes of protein, intracellular and extracellular, are encoded by genes which contain a promoter region coupled to a coding region. Genes encoding extracellularly directed proteins differ from those encoding intracellular proteins in that the portion of the coding region nearest to the promoter (which is the first part to be transcribed by RNA polymerase) encodes the signal peptide portion of the protein. The nucleotide sequence encoding the signal peptide, hereafter denoted the signal peptide coding region, is operationally part of the coding region per se.

SUMMARY OF THE INVENTION

In the present invention, from one aspect, a promoter region associated with a coding region in filamentous fungus such as *A. niger, A. nidulans* or a related species is identified and isolated, appropriately joined in a functional relationship with a second different coding region, outside the cell, and then re-introduced into a host filamentous fungus using an appropriate vector. Then the host cells express the protein of the second coding region, under the control of the introduced promoter region. The second coding region may be one which is foreign to the host species, in which case the host will express and in some cases secrete a protein not naturally expressed by the given host. Alternatively, the second coding region may be one which is natural to the host, in which case it is associated with a promoter region different from the promoter region with which it naturally associates in the given host, to give modified or enhanced protein expression and secretion.

In another aspect, where the second coding region encodes a protein which is normally secreted then the second coding region itself will contain a sequence of nucleotides at its 5' terminus i.e. a signal peptide coding region, which will result, following transcription and translation, in the presence of a signal peptide at the amino terminus of the protein product. The signal peptide will be recognized by the fungal host and the protein product will then be directed into the secretory pathway of the cell.

In another aspect, the present invention provides an appropriate DNA sequence coding for a signal peptide i.e. a signal peptide coding region, which is recognized by filamentous fungi preferably of the ascomycetes class so as to signal secretion of a protein encoded within the coding region. As indicated above, these signal peptide coding regions may be coupled to a coding region which encodes a protein naturally retained intracellularly, in order to elicit secretion of that protein. Normally secreted proteins are encoded by coding regions which usually contain these signal peptide coding regions naturally so that incorporation of a signal peptide coding region is not usually necessary. Nevertheless, the signal peptide coding regions of the present invention may be substituted for the naturally occurring such sequence, if desired. Accordingly, where a signal peptide coding region is inserted into a vector to obtain secretion, it will be foreign to the coding region.

The present invention provides the ability to introduce foreign coding regions into filamentous fungi along with promoters to arrange for the host fungi to express different proteins. It also provides the ability to regulate transcription of the individual genes which occur naturally therein or foreign genes introduced therein, via the promoter region which has been introduced into the host along with the gene. For example, the promoter region naturally associated with the alcohol dehydrogenase I (alcA) gene and the aldehyde dehydrogenase (aldA) genes of *A. nidulans* are regulatable by means of ethanol, threonine, or other inducing substances in the extracellular medium. This effect is dependent on the integrity of a gene known as alcR. When the alcA or aldA promoter region is associated with a different structural gene in Aspergillus or the like, in accordance with the present invention, similar regulation of the expression of the different genes by ethanol or other inducers can be achieved.

As a further example, the promoter region naturally associated with the glucoamylase gene in *Aspergillus niger* and used in embodiments of the present invention is positively induced with starch and other sugars.

In another aspect, the present invention provides a DNA segment which contains a promoter region in operative association with a signal peptide coding region and which permits introduction of a region coding for a desired protein at a position 3' of and in reading frame with the signal peptide coding region when the introduced coding region does not contain a signal peptide coding region. The promoter/signal segment is suitably provided with a flanking restriction site to allow precise coupling of the protein coding region to the signal peptide coding region.

In another aspect, the present invention provides a genetic vector capable of introducing the segment carrying the promoter and signal peptide coding region into the genome of a filamentous fungus host. The vector may also include a protein coding region either native to or foreign to the host filamentous fungus.

Thus the present invention, provides DNA sequences active as promoter regions in association with coding regions in cells of filamentous fungi such as *Aspergillus niger, Aspergillus nidulans* and the like.

The present invention thus also provides a novel composition of matter comprising a DNA sequence active as a promoter region in cells of filamentous fungi, and a coding region chemically bound to said DNA sequence in operative association therewith, said coding region being capable of expression in a filamentous fungus host under influence of said DNA sequence.

The present invention further provides a process of genetically modifying a filamentous fungus host cell which comprises introducing into the host cell, by means of a suitable plasmid vector, a coding region capable of expression in the Aspergillus host cell and a promoter region active in the Aspergillus host cell, the coding region and the promoter being chemically bound together and in operative association with one another.

DESCRIPTION OF THE PREFERRED EMBODIMENTS

Preferred hosts according to the invention are the filamentous fungi of the ascomycete class, most preferably Aspergillus sp. including *A. niger, A. nidulans* and the like.

In the preferred form of the invention the promoter region associated with either the *Aspergillus niger* glucoamylase gene or the promoter region associated with the alcohol dehydrogenase I gene or aldehyde dehydrogenase gene associated with *Aspergillus nidulans* is obtained and used in preparing an appropriate vector plasmid.

Either or all of these promoter regions is regulatable in the host cell by the addition of the appropriate inducer substance. In alcA and aldA, this induction is mediated by a third gene, alcR which is controlled via the promoter. Multiple copies of alcR may be used to increase the expression of alcA, aldA and related sequences. In some instances the gene can be repressed, for example by utilizing high levels of glucose, (and some other carbon sources) in the medium to be used for growth of the host. The expression of the product encoded by the coding region is then delayed until after the end of the cell growth phase, when all of the glucose has been consumed and the gene is derepressed. The inducer may be added at this point to enhance the activity of the gene.

The destination of the protein product of the coding region which has been selected to be expressed under the control of the promoter described above is determined by the nucleotide sequence of that coding region. As mentioned, if the protein product is naturally directed to the extracellular environment, it will inherently contain a secretion signal coding region. Protein products which are normally intracellularly located lack this signal peptide.

Thus, for the purposes of the present disclosure it is to be understood that a "coding region" encodes a protein which is either retained intracellularly or is secreted. (This "coding region" is sometimes referred to in the art as a structural gene i.e. that portion of a gene which encodes a protein.) Where the protein is retained within the cell that produces it, the coding region will usually lack a signal peptide coding region. Secretion of the protein encoded within the coding region can be a natural consequence of cell metabolism in which case the coding region inherently contains a signal peptide coding region linked naturally in translation reading frame with that segment of the coding region which encodes the secreted protein. In the alternative, the coding region may contain a signal peptide coding region which is foreign to that portion of the coding region which encodes the secreted protein. This foreign signal peptide coding region may be required where the coding region does not naturally contain a signal peptide coding region or it may simply replace the natural signal peptide coding region in order to obtain enhanced secretion of the desired protein with which the natural signal peptide is normally associated.

In accordance with another preferred aspect of the invention, therefore, a signal peptide coding region is provided, if required i.e. when the coding region which has been selected to be expressed under the control of the promoter described above does not itself contain a signal peptide coding region. The signal peptide coding region used is preferably either one which is associated with the Aspergillus niger glucoamylase gene or a synthetic signal peptide coding region which is made in vitro and used in the preparation of an appropriate vector plasmid. Most preferably, these signal peptide coding regions are modified at one or both termini to permit ligation thereof with other components of a vector. This ligation is effected in such a way that the signal peptide coding region is interposed between the promoter region and the protein encoding segment of the coding region such that the signal peptide coding region is in frame with that segment of the coding region which encodes the mature, functional protein.

BRIEF REFERENCE TO THE DRAWINGS

FIG. 1 is an illustration of the base sequence of the DNA constituting the structural genes and promoter regions of the alcohol dehydrogenase (alcA) gene (upper lines) and aldehyde dehydrogenase (ald A) gene (lower lines) of Aspergillus nidulans.

FIG. 5 (Parts A–C) is an illustration of a selection of synthetic linker sequences for insertion into plasmid pGL2;

FIG. 6 is an illustration of the nucleotide sequence of a fragment of pGL2;

FIG. 8 is an illustration of the nucleotide sequence of a fragment of pGL2BIFN;

FIG. 11 represents the nucleotide sequence of a fragment of pALCA1SIFN;

FIG. 12 illustrates the plasmid map of pGL2CENDO;

FIG. 13 represents the nucleotide sequence of a fragment of pGL2CENDO;

FIG. 14 represents a plasmid map of pALCA1SENDO;

FIG. 15 represents the nucleotide sequence of a fragment of pALCA1SENDO;

FIG. 17 represents the nucleotide sequence of a segment of pALCA1AMY shown in FIG. 16.

DETAILED DESCRIPTION OF PREFERRED EMBODIMENTS

Figure 2:
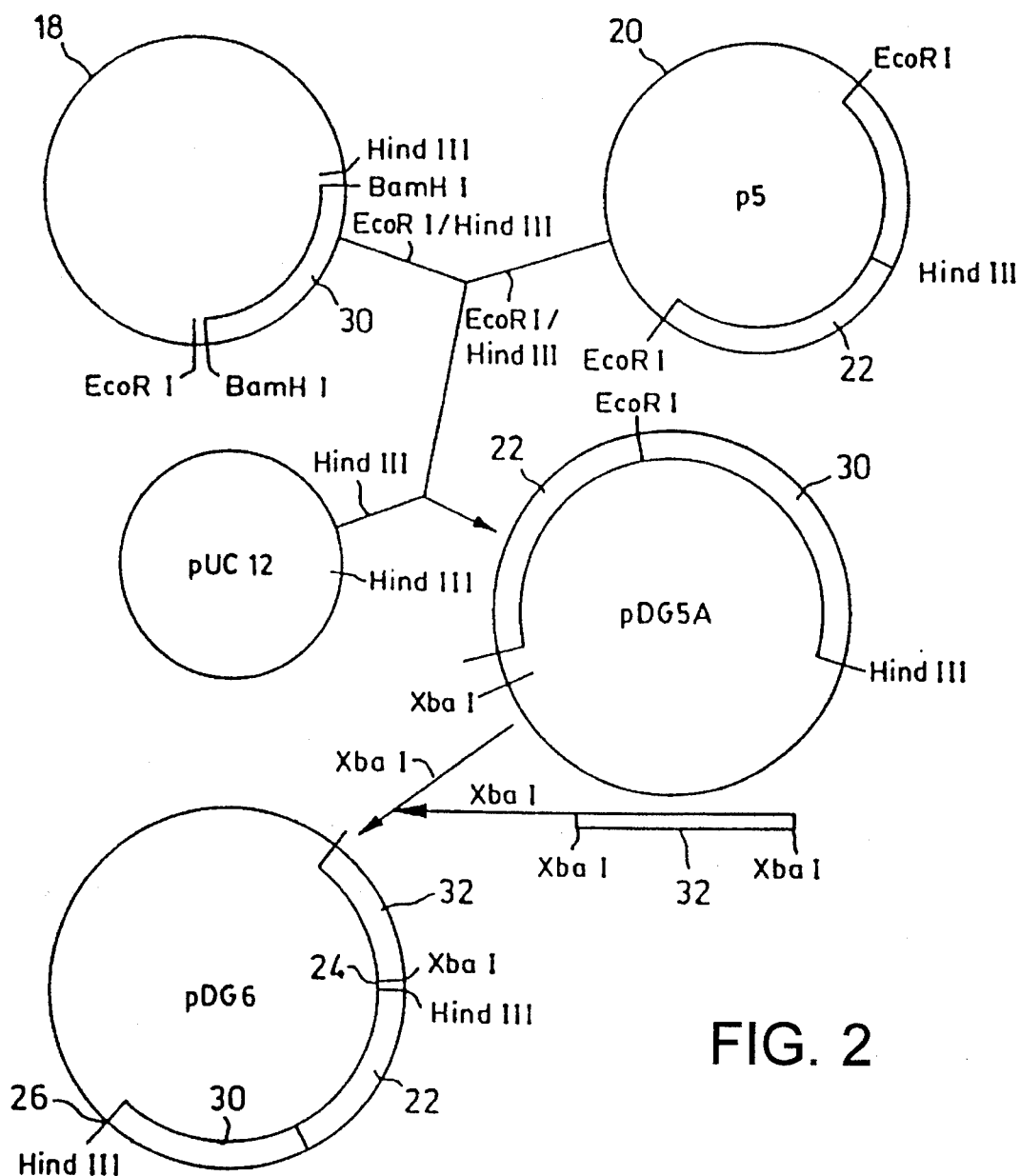
FIG. 2 is a diagrammatic illustration of a process of constructing a vector and of transforming a filamentous fungal cell therewith, according to the present invention.

In the present invention, an appropriate promoter region of a functioning structural gene in A. niger or A. nidulans or the like is identified. For this purpose, cells of the chosen species are induced to express the selected protein e.g. alcA and from these cells is isolated the messenger RNA. One portion thereof, as yet unidentified codes for alcA. Complementary DNA for the fragments is prepared from the mRNA fragments and cloned into a vector. Messenger RNA isolated from induced A. nidulans was size fractionated to enrich for alcA sequences, end labelled and hybridized to the cDNA clones made from the alcA$^+$ strain. That clone containing the cDNA which hybridized to alcA$^+$ mRNA contains the DNA copy of the alcA mRNA. This piece is hybridized to a total DNA gene bank from the chosen Aspergillus species, to isolate the selected structural gene e.g. alcA and its flanking regions. The aldA structural gene was isolated using analogous procedures.

The coding region starts at its 5' end, with a codon ATG coding for methionine, in common with other structural genes and proteins. Where the amino acid sequence of the expressed protein is known, the DNA sequence of the coding region is readily recognizable. Immediately "upstream" of the ATG codon is the leader portion of the messenger RNA preceded by the promoter region.

With reference to FIG. 1, this shows portion of the total DNA sequence from A. nidulans, with conventional base notations. The portion shown in the upper lines contains the promoter region and a part of the coding region alcA encoding alcohol dehydrogenase I, and the portion shown in the lower lines contains the promoter region and a part of the structural gene encoding aldehyde dehydrogenase i.e. aldA. The amino acid sequence of these two enzymes is known in other species. From these, the region 10 is recognisable as the coding regions. Each starts at its 5' ("upstream") end with methionine codon ATG at 12, 12'. The appropriate amino acid sequences encoded by the structural genes are entered below the respective rows on FIG. 1, in conventional abbreviations. Immediately upstream of codon 12 is the messenger RNA leader and the promoter region associated with the coding region, the length of which, in order to contain all the essential structural features enabling it to function as a promoter, now needs to be determined or at least estimated. FIG. 1 shows a sequence of 800 bases in each case, upstream from the ATG codon 12.

It is predictable from analogy with other known promoters that all the functional essentials are likely to be contained within a sequence of about 1000 bases in length, probably within the 800 base sequence illustrated, and most likely within the first 200–300 base sequence, i.e. back to position 14 on FIG. 1. An essential function of a promoter region is to provide a site for accurate initiation of transcription, which is known to be a TATA box sequence such as 5'TATATA3'. Such a sequence is found at 16 on the alcA promoter sequence of FIG. 1. Another function of a promoter region is to provide, along with the coding region, an appropriate DNA sequence adjacent to the coding region sequence for regulation of the gene transcription, e.g. a binding site for a regulatory molecule which enhances gene transcription, or for rendering the gene active or inactive. Such regulator regions are within the promoter region illustrated in FIG. 1.

The precise upstream 5' terminus of the DNA sequence used herein as a promoter region is not critical, provided that it includes the essential functional sequences as described herein. Excess DNA sequences beyond the 5' terminus are unnecessary, but unlikely to be harmful in the present invention.

Having determined the extent of sequence containing all the essential functional features to constitute a promoter region from the given gene, by techniques described herein, the next step is to cut the DNA chain at a convenient location downstream of the promoter region terminus and to remove the structural gene region, to leave basically a sequence comprising the promoter region and sometimes part of the messenger RNA leader. For this purpose, appropriately positioned restriction sites are to be located, and then the DNA treated with the appropriate restriction enzymes to effect scission. Restriction sites are recognizable from the sequences illustrated in FIG. 1. For the upstream cutting, a site is chosen sufficiently far upstream to include in the retained portion all of the essential functional sites for the promoter region. As regards the downstream scission, no restriction site presents itself exactly at the ATG codon 12. The closest downstream restriction site thereto us the sequence GGGCCC at 22, at which the chain can be cut with restriction enzyme Apa I. If desired, after such scission, the remaining nucleotides from location 22 to location 12 can be removed, in stepwise fashion, using an exonuclease. With knowledge of the number of such nucleotides to be removed, the exonuclease action can be appropriately stopped when the location 12 is passed. In many cases, however, a residue of a portion of the structural gene on the 5' terminus of the promoter region is not harmful to and does not significantly interfere with the functioning of the promoter region, so long as the reading frame of the base triplets is maintained.

FIG. 2 of the accompanying drawings illustrates diagrammatically the steps in a process of preparing Aspergillus transformants according to the present invention. On FIG. 2, 18 is a recombinant plasmid containing the endogluconase (cellulase) coding region 30 from *Cellulomonas fimi*, namely a BamHI endoglucanase fragment from *C. fimi* in known vector M13MP8. It contains relevant restriction sites for EcoRI Hind III and BamHI as shown as well as others not shown and not of consequence in the present process. Item 20 is a recombinant plasmid designated p5, constructed from known *E. coli* plasmid pBR322 and containing an EcoRI fragment of *A. nidulans* containing the alcA promoter region prepared as described above, along with a small portion of the alcA coding region, including the start codon ATG. It has restriction sites as illustrated, as well as other restriction sites not used in the present process and so not illustrated. Plasmid p5 contains a DNA sequence 22, from site EcoRI (3') to site Hind III (5'), which is in fact a part of the sequence illustrated on FIG. 1, upper row, from base 240 (the sequence GAATTC thereat constituting an EcoRI restriction site) to base −580 thereon. Sequence 22 in plasmid 20 is approximately 2 kb in length.

The plasmids 18 and 20 are next cut with restriction enzymes EcoRI and Hind III, and ligated to plasmid pUC12, so as to excise the alc A promoter region and the endoglucanase (cellulase) gene and prepare a novel construct pDG5A containing these sequences on pUC12, as shown in FIG. 2. Plasmid pUC12 is a known, commercially available *E. coli* plasmid, which replicates efficiently in *E. coli*, so that abundant copies of pDG5A can be made if desired. Novel construct pDG5A is isolated from the other products of the construct preparation. Next, construct pDG5A is provided with a selectable marker so that subsequently obtained transformants of Aspergillus into which the construct has successfully entered can be selected and isolated. In the case of Arg B- Aspergillus hosts, one can suitably use an Arg B gene from *A. nidulans* for this purpose. The Arg B gene codes for the enzyme ornithine transcarbamylase, and strains containing this gene are readily selectable and isolatable from Arg B- strains by standard plating out and cultivation techniques. Arg B- strains will not grow on a medium not containing arginine.

To incorporate a selectable marker, in this embodiment of the invention as illustrated in FIG. 2, construct pDG5A may be ligated with the Xba I fragment 32 of plasmid pDG3 (see U.S. patent application Ser. No. 06/678,578 Buxton et al, filed Dec. 5, 1984) which contains the Arg B+gene from *A. nidulans* using Xba I, to form novel construct pDG6, which contains the endoglucanase coding region, the alcA promoter sequence and the Arg B gene. Plasmid pDG6 can now be used in transformation, to prepare novel Aspergillus mutant strains containing an endoglucanase coding region under the control of alcA promoter.

Figure 3:
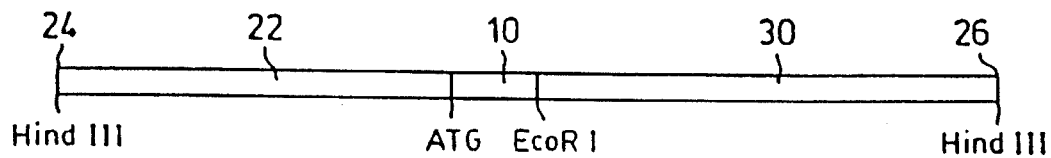
FIG. 3 is a linear representation of a portion of the plasmid pDG6 of FIG. 2.

FIG. 3 shows in linear form the diagrammatic sequence of the functional portion of construct pDG6, from the Hind III site 24 to the Hind III site 26. It contains the alcA promoter region, the ATG codon 12 and a small residual portion 28 of the alcA structural gene 10 as shown in FIG. 1, followed by the cellulase gene 30 derived from plasmid 18.

Figure 4:
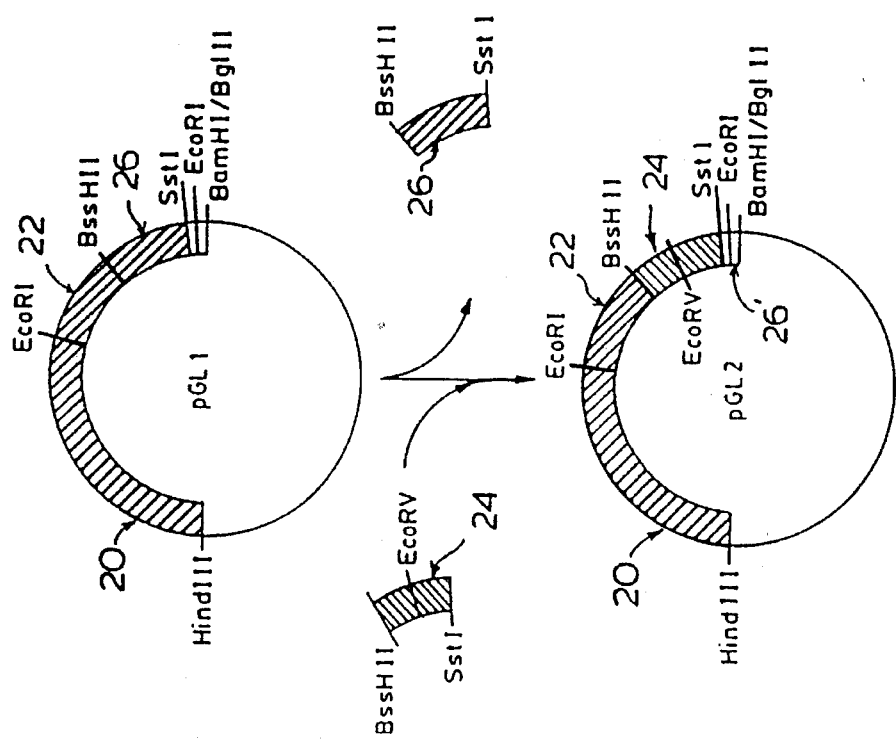
FIG. 4 is a diagrammatic illustration of the plasmid maps of pGL1 and pGL2.
Figure 9:
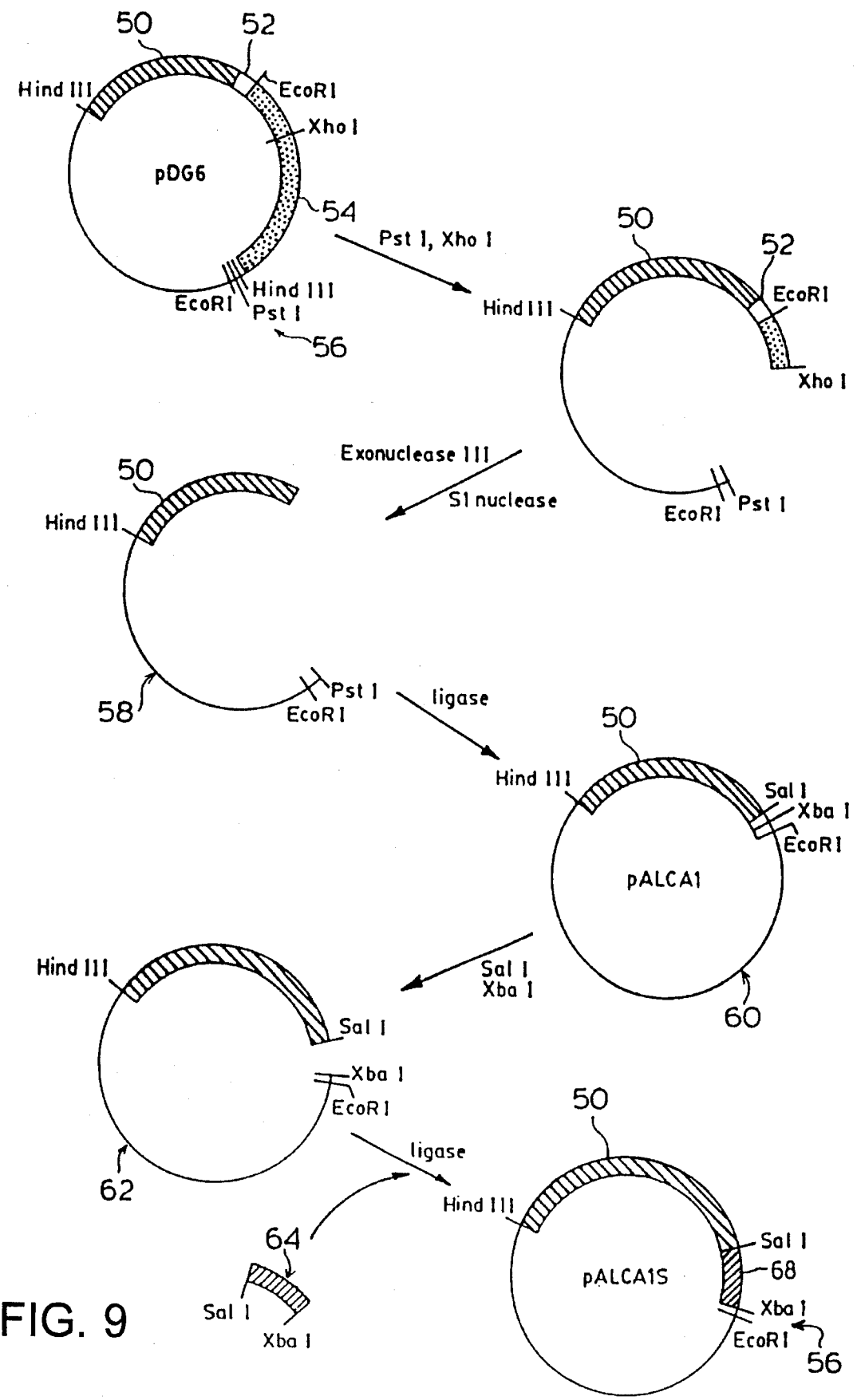
FIG. 9 illustrates plasmid pALCA1S and a method for its preparation.

Plasmids pGL2 and pALCA1S as depicted in FIG. 4 and 9 represent particularly preferred cloning vectors for introduction of protein coding regions, promoter sequences and signal peptide coding regions into either *A. niger* or *A. nidulans*. These vectors provide for introduction of entire coding regions which are foreign to these fungi and for introduction of protein encoding segments which are foreign to either or both of the promoter region and signal peptide coding region integrated in these vectors.

Considering firstly the vector plasmid pGL2, reference is made to FIG. 4 showing a map of the plasmid with relevant restriction sites indicated throughout the diagrams, the restriction sites illustrated comprising those sites which bear on the manner by which the plasmid or vector is produced or may be manipulated according to the invention. Further sites may be present but are not considered relevant to the preferred embodiments shown and described herein.

pGL2 comprises the promoter region 20 of the glucoamylase gene native to *A. niger* the promoter region being situated between restriction sites Hind III and BssH II. Also comprised within region 20 is the genetic sequence coding for the signal sequence 22 of the glocoamylase structural gene, the signal sequence 22 being located downstream of the promoter 20. Cloned within the unique BssH II and Sst I sites i.e. downstream of the signal sequence 22 is a synthetic linker sequence 24 designed so as to permit insertion of a desired structural gene without altering the reading frame of the gene so inserted.

The synthetic linker component of pGL2 is preferably of one of the following three nucleotide constructions donoted A, B or C as defined in FIGS. 5A, 5B and 5C, respectively.

Each of the synthetic linker sequence shown in FIGS. 5A, 5B and 5C makes available an Eco RV restriction site and a Bgl II/Xho II restriction site either of which may be used for insertion of the structural gene. Moreover, it will be noted that all of the sequences provides for three reading frames as evidenced by the amino acid sequences appearing thereunder. The arg-ala amino acid sequence at the start is constant in each oligonucleotide and is identical to the amino acids flanking the signal peptide sequence cleavage site in the glucoamylase gene. The addition of one, two or three "A" residues in the nucleotide sequence following arg-ala provides the three reading frames necessary as shown by the variable amino acid sequence following arg-ala. One advantage of such sequence resides in their capacity to accept the structural gene as a component of the vector plasmid without altering the reading frame of that gene thereby retaining, in the expressed protein, the proper amino acid sequence.

Further, each synthetic linker sequence A, B and C is flanked by "sticky ends" which are complementary to those ends provided by cuts of the plasmid pGL2 shown in FIG. 4.

The signal sequence 22 located upstream of the linker sequence 24 i.e. upstream of the BssH II site, has the nucleotide sequence as shown below:

Chart I

| ATG | TCG | TTC | CGA | TCT | CTA | CTC | CCC | CTG | AGC | GGC | CTC | GTC | TGC |
|-----|-----|-----|-----|-----|-----|-----|-----|-----|-----|-----|-----|-----|-----|
| met | ser | phe | arg | ser | leu | leu | ala | leu | ser | gly | leu | val | cys |
| ACA | GGG | TTG | GCA | AAT | GTG | ATT | TCC | AAG | CGC | | | | |
| thr | gly | leu | ala | asn | val | ile | ser | lys | arg | | | | |

This signal sequence was excised from the glucoamylase gene indigenous to *A. niger* according to methods described hereinafter. It will be noted that the restriction site for BssH II is located near the 3' terminus of the signal peptide sequence. It will be further noted that the 5' terminus of each of the synthetic linker sequences illustrated in FIGS. 5A–5C provides a nucleotide sequence which provides a "sticky end" which when ligated to the 3' end of the signal peptide coding region cut with the same enzyme, results in a fragment in which the amino acid sequence encoded by the signal peptide sequence is in frame with the coding region chosen to be expressed and may function in its intended manner i.e. to direct secretion of the expressed protein encoding segment of the coding region which may be inserted at an appropriate position e.g the Eco RV restriction site, within the synthetic linker 24. This depends on the choice of the correct vector (pGLA,B or C).

The promoter region 20 of pGL2 is also derived from the glucoamylase gene indigenous to *A. niger*. In particular, a genetic fragment containing both the promoter region and the signal peptide sequence for the *A. niger* glucoamylase gene was excised from an appropriate gene bank, as described hereinafter.

The invention is further described and illustrated by the following specific, non-limiting examples.

EXAMPLE 1

The vector construct pDG6 shown in FIG. 2 was prepared following the process scheme illustrated in FIG. 2, using standard routine ligation and restriction techniques. An EcoRI-Hind III fragment containing the promoter region of the alcA gene, about 2,000 bases long was used. With reference to the sequence on FIG. 1 upper row, it extends from base 240 to 2,000 bases upstream, approximately. Then the construct pDG6 was introduced into Arg B- mutant cells of *Aspergillus nidulans* as follows:

500 mls of complete media (Cove 1966)+0.02% arginine +$10^{-5}$% biotin in a 2 l conical flask was innoculated with $10^5$ conidia/ml of an A. nidulans Arg B- strain and incubated at 30° C., shaking at 250 rpm for 20 hours. The mycelia were harvested through Whatman No. 54 filter paper, washed with sterile deionized water and sucked dry. The mycelia were added to 50 ml of filter sterile 1.2M MgSO$_4$ 10 mM potassium phosphate pH 5.8 in a 250 ml flask to which was added 20 mg of Novozym 234 (Novo Enzyme Industries), 0.1 ml (m=15000 units) of β-glucuronidase (Sigma) and 3 mg of Bovine serum albumin for each gram of mycelia. Digestion was allowed to proceed at 37+ C. with gentle shaking for 50–70 minutes checking periodically for spheroplast production by light-microscope. 50 mls of sterile deionised water was added and the spheroplasts were separated from undigested fragments by filtering through 30 um nylon mesh and harvested by centrifuging at 2500 g for 5 minutes in a swing out rotor in 50 ml conical bottom tubes, at room temperature. The spheroplasts were washed, by resuspending and centrifuging, twice in 10 mls of 0.6M KCl. The number of spheroplasts was determined using a hemocytometer and they were resuspended at a final concentration of $10^8$/ml in 1.2M Sorbitol, 10 mM Tris/HCl, 10 mM CaCl$_2$ pH 7.5 . Aliquots of 0.4 ml were placed in plastic tubes to which DNA pDG6 (total vol. 40 μl in 10 mM Tris/HCl 1 mM EDTA pH 8) was added and incubated at room temperature for 25 minutes. 0.4 ml, 0.4 ml then 1.6 ml aliquots of 60% PEG4000, 10 mM Tris/HCl, 10 mM CaCl$_2$ pH 7.5 were added to each tube sequentially with gentle, but thorough mixing between each addition, followed by a further incubation at room temperature for 20 minutes. The transformed spheroplasts were then added to appropriately supplemented minimal media 1% agar overlays, plus or minus 0.6M KCl at 45° C. and poured immediately onto the identical (but cold) media in plates. After 3–5 days at 37° C. the number of colonies growing was counted (F. Buxton et al), Gene 37, 207–214 (1985)). The method of Yelton et al [Proc. Nat'l Acad. Sci. U.S.A 81; 1370–1374 (1980)] was also used.

The colonies were divided into two groups. Threonine (11.9 g/Liter) and fructose (1 g/Liter) were added to the incubation medium for one group to induce the cellulase gene incorporated therein. No inducer was added to the other group, which were repressed by growth on minimal media with glucose as sole carbon source. Both groups were assayed for general protein production by BioRad Assay, following cultivation, filtering to separate the mycelia, freeze drying, grinding and protein extraction with 20 mM Tris/HCl at pH 7.

To test for production of cellulase, plates of Agar medium containing cellulase (9 g/Lt, carboxymethylcellulose) were prepared, and small pieces of glass fibre filter material, isolated from one another, and 75 μg of total protein from one of the transconjugants was added to each of the filters. The plates were incubated overnight at 37° C. The filters were then removed, and the plates stained with congo red to determine the locations where cellulase had been present in the total protein on the filters, as evidenced by the breakdown of cellulase in the agar medium below. The plates were de-stained, by washing with 5M NaCl in water, to detect the differences visibly.

Of four transformants induced with threonine and fructose, three clearly showed the presence of cellulase in the total protein product. The non-induced, glucose repressed transformants did not show evidence of cellulase production.

Three control transformants were also prepared from the same vector system and strains, but omitting the promoter sequence. None of them produce cellulase, with or without inducers. The presence of *C. fimi* endoglucanase coding region was verified by the fact that medium from threonine-induced transformed strains showed reactivity with a monoclonal antibody raised against *C. fimi* endoglucanase. This monoclonal antibody showed no cross-reactivity with endogenous *A. nidulans* proteins in control strains.

EXAMPLE 2

Figure 16:
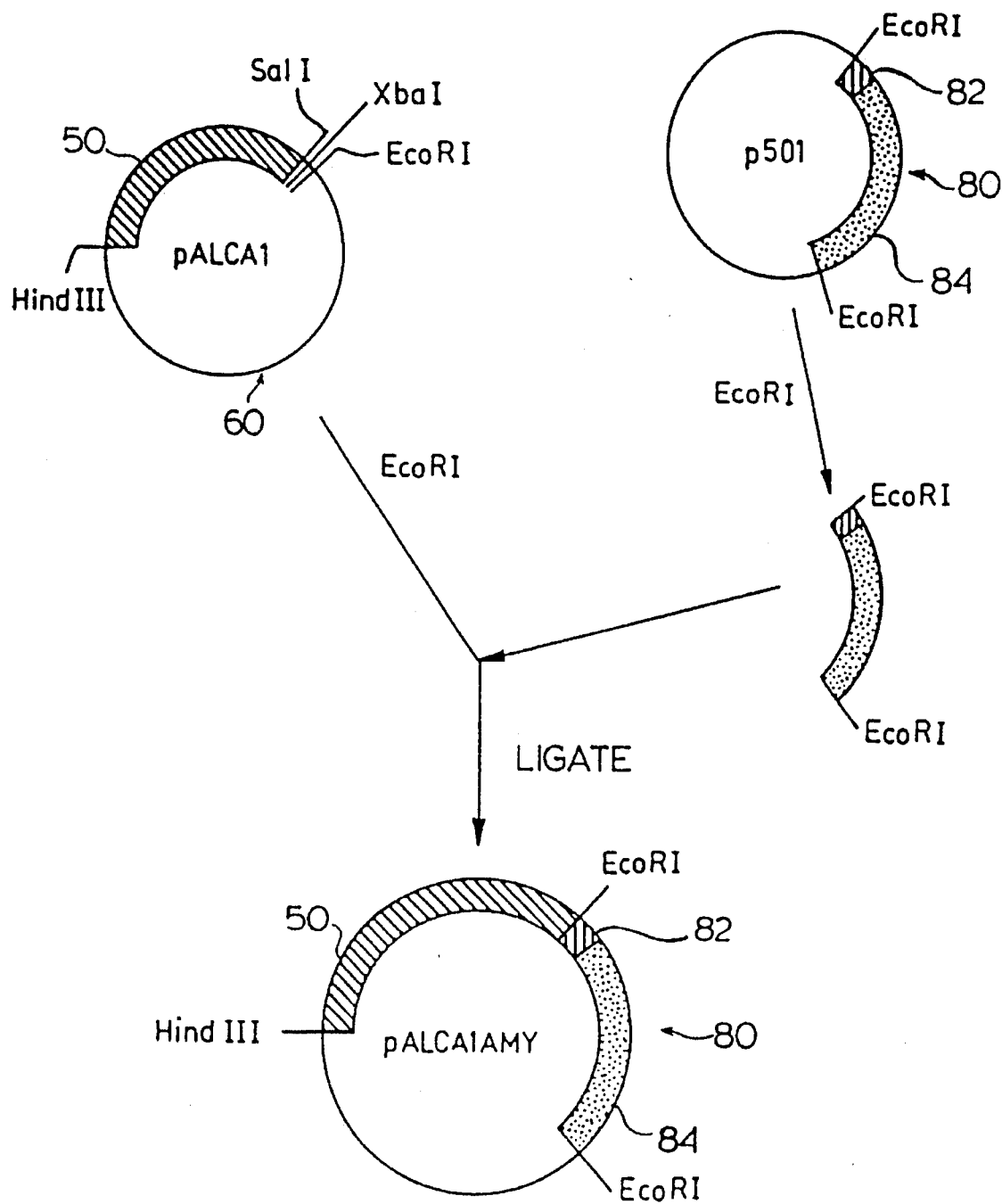
FIG. 16 illustrates plasmid pALCA1AMY and a method for its preparation.

The vector construct pALCAlAMY was prepared as indicated in FIG. 16, using standard routine ligation and restriction techniques. In particular, vector pALCA1 60 containing a Hind III-EcoRI segment in which the *A. nidulans* alcohol dehydrogenase 1 promoter 50 is located (as described previously), was cut at its EcoRI site in order to insert the coding region of the wheat α-amylase gene 80 contained within an EcoRI-EcoRI fragment defined by plasmid p501 (see S. J. Rothstein et al, *Nature*, 308, 662–665 (1984)). As wheat α-amylase is a naturally secreted protein, its coding region 80 contains a signal peptide coding region 82 and a segment 84 which encodes mature, secreted α-amylase. Ligation of coding region 80 within the EcoRI-cut site of pALCAl provides plasmid pALCAlAMY in which the AlcA promoter is operatively associated with the α-amylase coding region. The correct orientation of the p501-derived α-amylase coding region within pALCAlAMY is confirmed by sequencing across the ligation site according to standard procedures. The nucleotide sequence of the promoter/coding region junction are shown in FIG. 17.

After transforming *A. nidulans* by the procedure described in example 1, samples of extracellular medium were taken from and applied to glass fibre filter papers placed on 1% soluble starch agar. The filters were removed after 8 hours at 37° C. and inverted onto beakers containing solid iodine (in a 50° C. water bath). Clear patches indicated starch degradation while the remaining starch turned a deep purple, thus confirming the presence of secreted α-amylase.

EXAMPLE 3

Production of Plasmid pGL2.
A) Source of promoter and signal peptide sequence

The glucoamylase gene of *A. niger* was isolated by probing a gene bank derived from DNA available in a strain of this microorganism on deposit with ATCC under catalogue number 22343. The probing was conducted using oligonucleotide probes prepared with Biosearch oligonucleotide synthesis equipment and with knowledge of the published amino acid sequence of the glucoamylase protein. The amino acid sequence data was "reverse translated" to nucleotide sequence data and the probes synthesized. The particular gene bank probed was a Sau 3A partial digest of the *A. niger* DNA described above cloned into the Bam HI site of the commercially available plasmid pUC12 which is both viable in and replicable in *E. Coli*.

A Hind III-Bgl II piece of DNA containing the glucoamylase gene was subcloned into pUC12. Subsequently, the location of the desired promoter region, signal peptide sequence and structural gene of glucoamylase was identified within pUC12 containing the sub-cloned fragment. The Eco RI fragment (22 and 26 in FIG. 4) was shown to contain a long, open translation reading frame when it was sequenced and the sequence data was analyzed using the University of Wisconsin sequence analysis programmes.

Results of analysis of the nucleotide sequence of part of the region of the glucoamylase gene between two Eco RI sites within the Hind III-Bgl II fragment are shown in FIG. 6. This region contains the glucoamylase promoter and the signal peptide sequence.

Within this fragment i.e. at nucleotides 97–102 is a "TATA box", namely the familiar sequence $^5$TATAAA$^3$' which provides a site required by many eukaryotic promoter regions for accuracte initiation of transcription (probably an RNA polymerase II binding site). Accordingly, the presence of at least a portion of the promoter region is confirmed. Further, it is predictable from analogy with other known promoter regions that all the functional essentials are likely to be contained within a sequence of about 1,000 bases in length and most likely within the first 200 bases upstream of the start codon for the coding region i.e. nucleotides 206–208 or "ATG", the codon for methionine. Thus, the promoter and transcript leader terminate at nucleotide 205. The identity of the beginning of the promoter region is less crucial although the promoter region must contain the RNA polymerase II binding site and all other features required for its function. Thus, whereas the Eco RI-Eco RI sequence is believed to represent the entire promoter region of the glucaomylase gene, the fragment used in plasmid pGL2 contains this fragment in the much larger Hind III- BamH I/Bgl II segment to ensure that the entire promoter region is properly included in the resultant plasmid.

On the basis that the amino acid sequence of mature glucoamylase is known (see Svensson et al, "Characterization of two forms of glucoamylase from Aspergillus niger", *Carlsberg Res. Commun*, 47, 55–69 (1982)), a nucleotide sequence of the signal peptide can be determined accurately. The signal peptide coding region of genes encoding secreted proteins is known to initiate with the methionine residue encoded by the ATG codon. Determination of a sufficient initial portion of the nucleotide sequence beyond i.e. 3' of the ATG codon provides information from which the amino acid sequence of that portion may be determined. By comparison of this amino acid sequence with the published amino acid sequence, the signal peptide can be identified as that portion of the glucoamylase gene which has no counterpart in the published sequence with which it was compared. The glucoamylase signal peptide coding region defined herein was previously confirmed using this method.

By the above methods, the Hind III-Bam HI/Bgl II fragment resulting from Sau 3A partial digestion and incorporated into pUC12 was confirmed to contain the following features of the glucoamylase gene: an initial, perhaps non-relevant section, the promoter region, the signal peptide coding region and the remaining portion of the coding region. This fragment, inserted into the pUC12 plasmid by scission with Hind III and Bam HI/Bgl II and ligation appears schematically in FIG. 4 as plasmid pGL1. This plasmid contains all of the features necessary for replication and the like in order to remain selectable and replicable in *E. Coli* and selectable in *A. niger*.

B) Construction of Plasmid pGL2

Using pGL1 as a precursor, plasmid vector pGL2 can be formed as shown in FIG. 4. The restriction site BssH II which immediately follows the 3' end of the signal sequence 22, is utilized together with the unique Sst I site following in order to insert the synthetic linker sequences defined in FIGS. 5A–5C herein. Thus, pGL1 is cleaved with both BssH II and Sst I thereby removing the 5' portion of the structural glucoamylase gene 26 contained therein. Thereafter a selected one of the synthetic leader sequences A through C having been designed so as to be flanked by BssH II/Sst I compatible ends is inserted and ligated, thereby generating plasmid pGL2. Depending on which of the three linker sequences is used i.e. A, B or C, the resultant plasmid will hereinafter be identified as pGL2A, pGL2B or pGL2C, respectively.

The synthetic linker sequences identified herein are each equipped with unique Eco RV and Bgl II restriction sites into which a desired protein coding region may be inserted. Once inserted, the resultant plasmid may be used to transform a host e.g. *A niger, A. nidulans* and the like. The presence of the promoter region and the signal peptide coding region both of which are recognized by the host, provide a means whereby expression of the protein coding region and secretion of the protein so expressed is made possible.

EXAMPLE 4

Use of Plasmid pGL2

An example of the utility of the plasmid pGL2 is described below with reference to FIG. 7, which shows schematically the construction of plasmid pGL2BIFN from pGL2B.

The plasmid pGL2B is prepared as described in general previously for pGL2 save that synthetic linker sequence "B" shown in FIG. 5B is inserted specifically. The reference numeral 24 has accordingly been modified in FIG. 7 to read "24B". In order to make available an opening in the vector pGL2B, the plasmid is cut with Eco RV at the site internal to linker 24B. The scission results in blunt ends which may be ligated with a fragment flanked by blunt ends using ligases known to be useful for this specific purpose.

Figure 7:
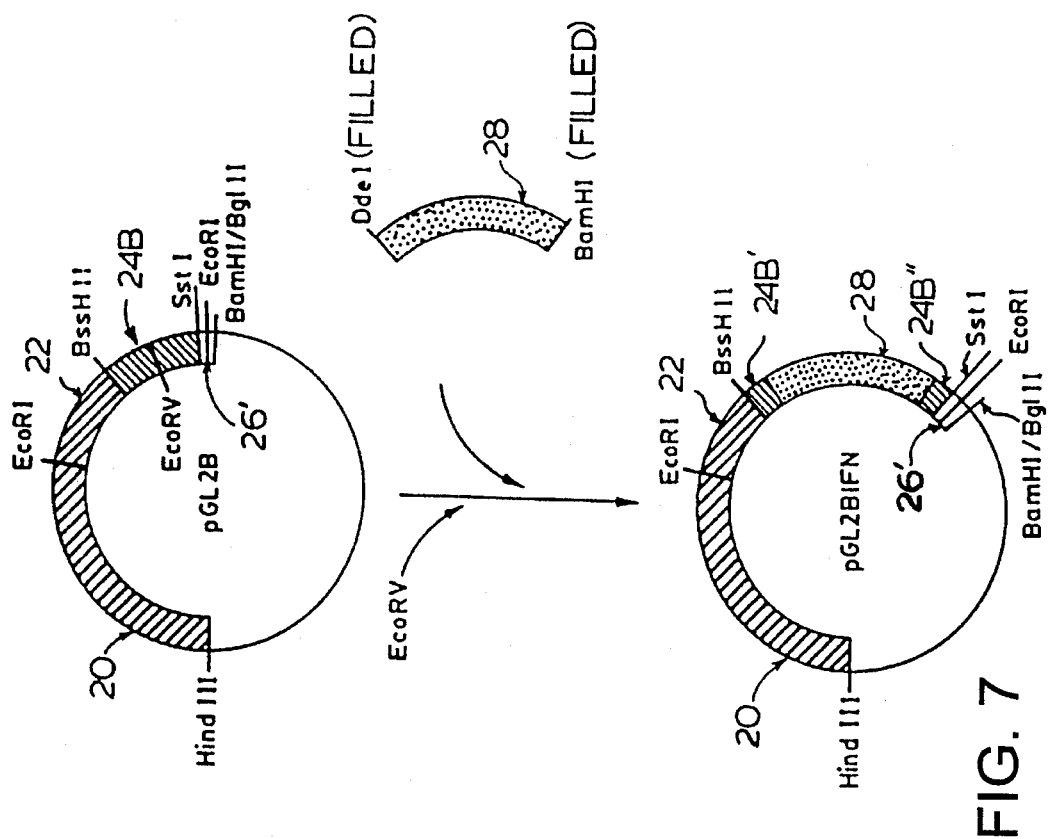
FIG. 7 is an illustration of plasmid map pGL2B and pGL2BIFN.

In the embodiment depicted in FIG. 7, a fragment 28 containing the coding region of human interferon 2 is inserted to create pGL2BIFN. Specifically, a Dde I-Bam HI fragment 28 containing the coding region coding for human interferon α2 was excised from plasmid pN5H8 (not shown) on the basis of the known sequence and restriction map of this gene.

The plasmid pN5H8 combines known plasmid pAT153 with the interferon gene at a Bam HI site. The interferon gene therein is described by Slocomb, et. al., "High level expression of an interferon α2 gene cloned in phage M13mp7 and subsequent purification with a monoclonal antibody" *Proceedings of the National Academy of Sciences*, U.S.A., Vo. 79 pp 5455–5459 (1982)

In order to anneal the sticky ends of the interferon fragment into the cut Eco RV site of pGL2B, the sticky Dde I and Bam HI ends are filled using reverse transcriptase and ligated with an appropriate ligase according to techniques standard in the art.

The advantage of selecting linker sequence B for insertion into pGL2 is manifest from FIG. 8 which shows the reading frame of the interferon 2 coding region and its relationship within the synthetic signal peptide sequence, in terms of nucleotide sequence and amino acid sequence, where appropriate.

FIG. 8 shows the promoter region 5' of the signal sequence joined with the glucoamylase signal peptide sequence beginning with the methionine codon ATG and ending with the lysine codon AAG at 32. In fact, although the signal peptide coding region extends one residue further i.e. to the CGC codon for arqinine at 34, this latter residue is comprised by the synthetic linker sequence engineered so as to compensate for the loss of the arginine residue during scission and ligation to insert the linker sequence. In this way, the genetic sequence of the signal remains undisturbed.

In a similar manner, the linker sequence provides for insertion of the interferon 2 coding region without altering the reading frame thereof. Cleavage of linker sequence B by Eco RV results in linker fragments B' and B" having blunt ends designated 36, 38, respectively. Excision of the interferon 2 coding region at Dde I site results, after filling in of the sticky ends created by the enzyme, in the desired nucleotide sequence without harming the sequence of that coding region. Ligation of the Eco RV-cleaved linker sequence with the interferon sequence filled at the Dde I site maintains the natural reading frame of the interferon coding region as evidenced by the triplet codon state between the linker portion B' and the interferon coding region. Had the linker A shown in FIG. 5A been chosen, which bears one less nucleotide than the linker B, the entire reading frame would have been shifted by one nucleotide resulting in a nonsense sequence. By selection of synthetic linker B, codons are made available between the signal peptide sequence and the interferon coding region which do not alter the reading frame of the coding region, when the blunt ended IF2 fragment is oriented correctly. The correct orientation is selected by sequencing clones with inserts across the ligation junction.

EXAMPLE 5

Expression and Secretion from *A. nidulans* Transformaned with pGL2BIFN

The plasmid pGL2BIFN was cotransformed i.e. with a plasmid containing Arg B+ gene as described more fully in U.S. patent application Ser. No. 678,578 filed Dec. 5, 1984 into an Arg B– strain of *A. nidulans* with a separate plasmid containing an arg B selectable marker. Arg B+ transformants were selected of which 18 of 20 contained 1–100 copies of the human interferon 2 coding region (as detected by Southern blot analysis).

Several transformants were grown on starch medium to induce the glucoamylase promoter and the extracellular medium was assayed for human IF α2 using the CellTech IF α2 assay kit.

All transformants exhibited some level of synthesis and secretion of assayable protein. Two controls, the host strain (not transformed) and one arg B$^+$ transformant with no detectable human IF α2 DNA showed no detectable synthesis of IF α2 protein. In a separate experiment, transformation of *A. niger*, rather than *A. nidulans*, with pGL2BIFN using, mutatis mutandis, the same procedure as described above, demonstrated the ability of *A. niger* to secrete IF α2.

Thus, although the promoter and signal regions of pGL2BIFN are derived from *A. niger* they are shown to be operative in both *A. nidulans* and *A. niger*.

In the present invention, use may be made of promoter regions other than the glucoamylase promoter region. Suitable for use are the promoter regions of the alcohol dehydrogenase I gene and the aldehyde dehydrogenase gene, illustrated in FIG. 1.

EXAMPLE 6

Construction of Plasmid pALCAIS

For use with the present example, the alcA promoter was employed as comprised within an 10.3 kb plasmid pDG6 deposited with ATCC within host *E. Coli* JM8 3 under accession number 53169. A plasmid map of pDG6 is shown in FIG. 9, to which reference is now made, to illustrate use of the alcA promoter.

pDG6 comprises the promoter region 50 of the alcA gene as well as a small 5' portion 52 of the alcA coding region 3' of the start codon, ligated to the endoglucanase structural gene 54. pDG6 further comprises a multiple cloning site 56 downstream of the *C. fimi* endoglucanase coding region 54.

To retrieve the alcA promoter region 50, pDG6 was cut with Pst I and Xho I removing the bulk of the endoglucanase coding region 54. In a second step, the linearized plasmid was resected in one direction in a controlled manner with exonuclease III (which will resect from XhoI but not PstI-cut DNA ends) followed by tailoring with nuclease S1. The resection was timed so that the enzyme removed nucleotides to a position 50 bases 5' of the alcA ATG codon, leaving the TATA box and messenger RNA start site intact.

Following resection, the vector 58 was religated (recircularized) creating vector 60 bearing Sal I-Xba I restriction sites immediately downstream of the promoter region 50. Cleavage of vector 60 with Sal I/Xba I permits introduction of a signal peptide coding region at an appropriate location within the vector.

The particular signal peptide coding region employed in the present example was synthesized to reproduce a typical signal peptide coding region identified according to standard procedures as described by G. Von Heijne in *Eur. J. Biochem.* 17–21, (1983). The synthetic signal was engineered so as to provide a 5' flanking sequence complementary to a Sal I cleavage site and a 3' flanking sequence enabling ligation with the Xba I restriction sequence.

The sequence of the synthetic secretion signal 64 is reproduced below:

```
Sal I
      TCGACATGTAC CGG TTC CTC GCC GTC ATC TCG GCC TTC CTC GCC ACT GCC TTC GCC AAG
1 ———————|——————————|——————————|——————————|——————————|——————————|——————————+ 59
          GTACATG GCC AAG GAG CGG CAG TAG AGC CGG AAG GAG CGG TGA CGG AAG CGG TTC

MetTyr  Arg Phe Leu Ala Val Ile Ser Ala Phe Leu Ala Thr Ala Phe Ala Lys
    Xba I
      T
60 ——————— 64
    AGA TC
    Ser Arg
```

The secretion signal per se begins with Met and ends with Ala (fourth occurrence).

Once generated, the synthetic sequence acting as signal is cloned into the Sal I-Xba I site of vector 62 resulting in plasmid pALCAlS which contains alcA promoter region 50, and synthetic peptide signal coding region 64. That the signal peptide coding region is inserted upstream of the multiple cloning site 56 is significant in that the site 56 allows for cloning of a variety of protein coding segments within this plasmid.

Accordingly, pALCAlS constitutes a valuable embodiment of the present invention.

EXAMPLE 7

Construction of Plasmid pALCAlSIFN

Figure 10:
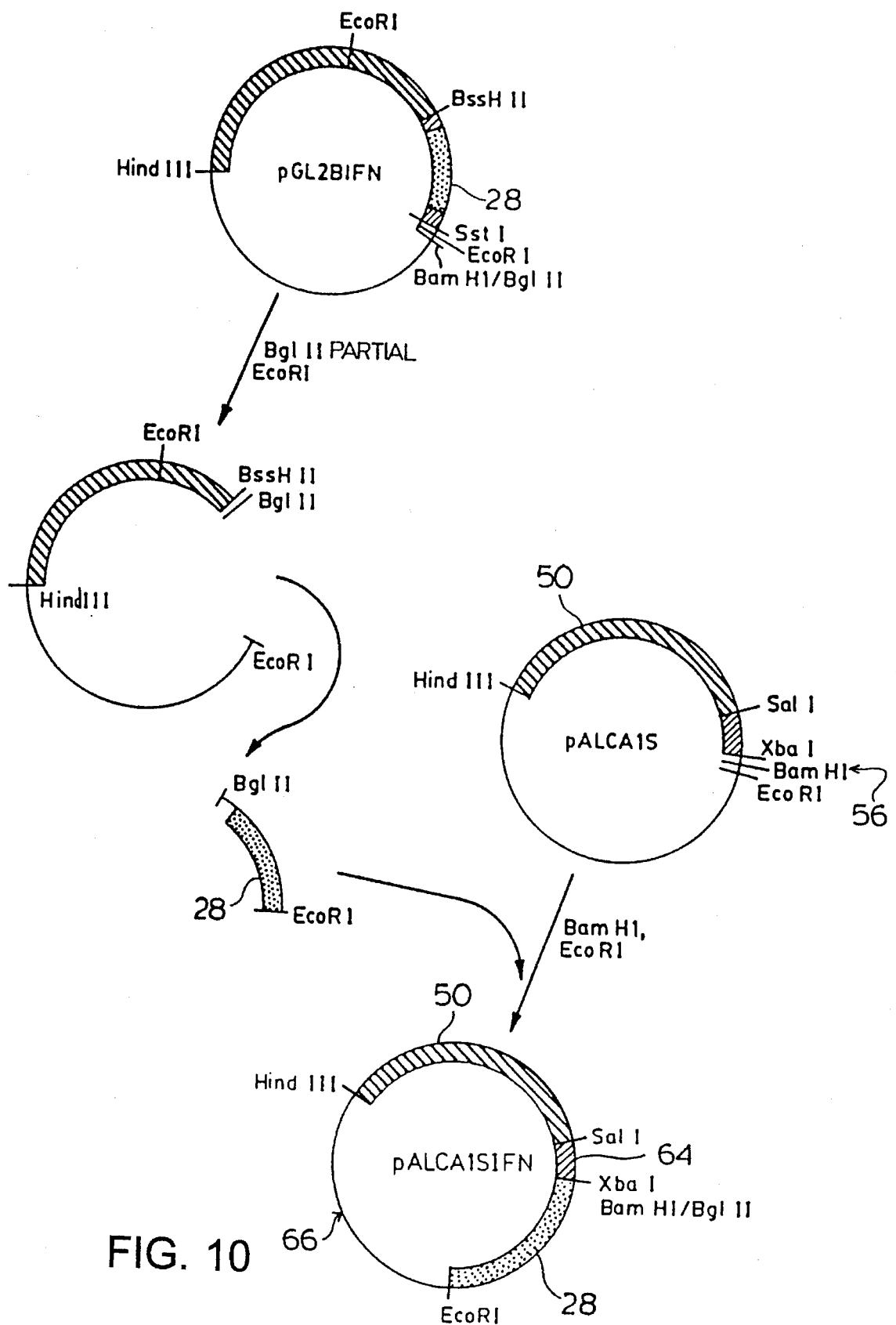
FIG. 10 illustrates the plasmid map of pALCA1SIFN and a method for its preparation.

As an example of the utility of pALCAlS, reference is made to FIG. 10 showing creation of pALCAlSIFN 66. This plasmid 66 comprises the promoter region 50 of the alcA gene and the synthetic signal peptide coding region 64 both of which are derived from pALCAlS (FIG. 9). In addition, it contains the structural gene 28 coding for human interferon α2 derived from pGL2BIFN.

To obtain the protein encoding segment, pGL2BIFN is cleaved with Eco RI and partially cleaved with Bgl II (because of the presence of internal Bgl II sites). Insertion of the protein coding region is accomplished by cleaving pALCAIS with Bam HI and Eco RI both of which are available in the multiple cloning site 56 and ligating this coding region therein, thereby creating pALCAlSIFN.

The nucleotide sequence of the resultant plasmid, from Hind III to Eco RI is shown in FIG. 11, indicating the sites of restriction endonuclease digestion. It will be noted from sheet 3 of FIG. 11 that the 1Fα2 coding region is in proper reading frame with the synthetic signal peptide coding region.

EXAMPLE 8

Expression and Secretion from *A. Nidulans* Transformed with Plasmid pALCAlSIFN

The plasmid pALCAlSIFN prepared as described above was co-transformed with *A. nidulans* to provide an arg B selectable marker, the arg B+ transformants selected and checked for the presence of the human interferon α2 coding region, then grown on a threonine-containing medium to induce the alcA promoter, all as described in example 3 above. The extracellular medium was assayed for human IF-2 using Cell Tech IF 2 assay kit. Eleven of twenty transformants showed secretion of interferon, induced in the presence of threonine, and repressed in the presence of glucose.

EXAMPLE 9 pGL2CENDO

In accordance with the procedures described in the previous examples, there was constructed a vector plasmid designated pGL2CENDO, from plasmid pGL2C, analagous to pGL2BIFN shown in FIG. 7, but containing the endoglucanase coding region in place of the interferon 2 coding region, and using the synthetic linker sequence "C" (FIG. 5C) in place of linker sequence "B". A Bam HI fragment containing the *C. fimi* endogluconase coding region was inserted into the Bgl II site. *A. nidulans* transformants were prepared with this vector plasmid, and showed starch regulated secretion of cellulase assayed as described in Example 1. The map of vector plasmid pGL2CENDO is shown in FIG. 12 of the accompanying drawings, in which 70 denotes the endoglucanase coding region (an endoglucanase from *Cellulomonas fimi*, described in connection with FIG. 2 and Example 1), 72 denotes the signal peptide coding region of the glucoamylase gene and 74 denotes the promoter region of the glucoamylase gene. The nucleotide sequence is shown in FIG. 13 and exemplifies that use of linker sequence C (FIG. 5C) retains the reading frame of the signal peptide coding region 72 and the endoglucanase coding region 70.

EXAMPLE 10

Construction of Plasmid pALCA1SENDO

In accordance with the procedures described in the previous examples, there was constructed a vector plasmid designated pALCA1SENDO by combining Eco RI-linearized plasmid pALCA1S as described in example 5 (FIG. 9) with an Eco RI fragment derived from plasmid pDG5B (see FIG. 2) (pDG5 with the orientation of the Hind III fragment reversed in pUC12) and containing the endoglucanase coding region. The map of pALCA1SENDO is shown in FIG. 14 and the nucleotide sequence of its pertinent region is shown in FIG. 15. In these figures, the promoter region derived from alc A is designated by numeral 50, the synthetic signal peptide coding region is designated 64 and the endoglucanase coding region is designated by reference numeral 30.

EXAMPLE 11

Expression and Secretion from A. nidulans Transformed with pALCA1SENDO and pGL2CENDO A. nidulans was co-transformed with an argB+ selectable marker and the plasmid pALCA1SENDO or pGL2CENDO prepared as described above. Of the co-transformants several showed varying levels of secretion of cellulase (i.e. endoglucanase) as assayed on carboxymethylcellulose plates and the monoclonal antibody test systems as described in example 1. Both plasmid transformants showed secretion which was controlled by the linked promoter. Plasmid pGL2CENDO was induced by starch and pALCA1SENDO was induced with threonine.

EXAMPLE 12

Expression and Secretion From A. niger Transformed with pGL2CENDO

A. niger was cotransformed with an arg B+ selectable marker and the plasmid pGL2CENDO. Several of the transformants showed varying levels of secretion of endoglucanase as assayed as described in example 1. This secretion was induced by the presence of starch in the medium.

Thus, the present invention provides a means for introducing a structural gene into a host which, when transformed, will secrete the desired protein. Particularly useful plasmids for this purpose are pALCA1S and pGL2 (A, B or C).

Useful transformation vectors derived from these plasmids include pALCA1SIFN, pGL2BIFN, pALCA1SENDO and pGL2CENDO. Cultures of each of these plasmids are currently maintained in a permanently viable state at the laboratories of Allelix Inc., 6850 Goreway Drive, Mississauga, Ontario, Canada. The plasmids will be maintained in this condition throughout the pendency of this patent application and, during that time, will be made available to the Commissioner of Patents and Trade Marks at his request. These plasmids have been deposited in accordance with the provisions of Budapest Treaty, with the American Type Culture Collection, located at 1201 Parklawn Drive, Rockville, Md. 20852, U.S.A., and have been accorded the Accession Numbers and deposits dates as set forth in the table below:

| Plasmid | Host | Accession # | Deposit Date |
| --- | --- | --- | --- |
| pDG6 | E. Coli JM83 | 53169 | June 7, 1985 |
| pGL2A | " | 53365 | Dec. 16, 1985 |
| pGL2B | " | 53366 | " |
| pGL2C | " | 53367 | " |
| pALCA1S | " | 53368 | " |
| pALCA1SENDO | " | 53370 | " |
| pALCA1SIFN | " | 53369 | " |
| pGL2BIFN | " | 53371 | " |
| pGL2CENDO | " | 53372 | " |
| pALCA1AHY | " | 53380 | Dec. 20, 1985 |

What is claimed is:

1. A DNA construct for use in transforming an Aspergillus host to obtain expression therein of a polypeptide, said DNA construct comprising promoter DNA for promoting transcription in Aspergillus and operably linked to DNA coding for said polypeptide to enable expression thereof in said Aspergillus host, said DNA coding for said polypeptide being foreign to said promoter DNA.

2. A DNA construct according to claim 1, wherein said Aspergillus host is *Aspergillus niger*.

3. A DNA construct according to claim 1, wherein said Aspergillus host is *Aspergillus nidulans*.

4. A DNA construct according to claim 1, wherein said promoter DNA comprises the alcA promoter native to *Aspergillus nidulans* operably linked to the *C. fimi* endoglucanase coding region.

5. A DNA construct according to claim 1, wherein the coding DNA is foreign to said Aspergillus host.

6. A DNA construct according to claim 1, further comprising a DNA fragment encoding a promoter-inducer substance.

7. A DNA construct according to claim 6, wherein said DNA fragment encodes alcR.

8. A DNA construct according to claim 7, wherein said promoter DNA is selected from the group consisting of the alcA and the aldA promoter of *Aspergillus nidulans*.

9. An Aspergillus strain which upon culturing expresses a polypeptide as a result of having been transformed by a DNA construct in which DNA coding for the polypeptide is linked operably to promoter DNA for promoting transcription in Aspergillus, said DNA coding for said polypeptide being foreign to said promoter DNA.

10. A strain according to claim 9, wherein said strain is a transformed Aspergillus species selected from the group consisting of *Aspergillus nidulans* and *Aspergillus niger*.

11. A strain according to claim 9, wherein the coding DNA is foreign to said Aspergillus strain.

12. A strain according to claim 9, wherein said promoter DNA comprises the alcA promoter native to *Aspergillus nidulans*.

13. A strain according to claim 10, which is an *Aspergillus niger* transformant.

14. A method for producing a polypeptide, said method comprising the step of culturing an Aspergillus strain transformed by a DNA construct in which DNA coding for a polypeptide is linked operably to promoter DNA for promoting transcription in Aspergillus, said DNA coding for said polypeptide being foreign to said promoter DNA.

15. A method according to claim 14, wherein the cultured strain is a transformed Aspergillus species selected from the group consisting of *Aspergillus nidulans* and *Aspergillus niger*.

16. A method according to claim 14, wherein the coding DNA is foreign to said Aspergillus strain.

17. A method according to claim 14, wherein said promoter DNA is selected from the alcA promoter of *Aspergillus nidulans* and the aldA promoter of *Aspergillus nidulans*.

18. A method according to claim 15, wherein said cultured strain is an *Aspergillus niger* transformant.

* * * * *

UNITED STATES PATENT AND TRADEMARK OFFICE
CERTIFICATE OF CORRECTION

PATENT NO. : 5,503,991
DATED : April 2, 1996
INVENTOR(S) : GWYNNE et al

It is certified that error appears in the above-identified patent and that said letters patent is hereby corrected as shown below:

Column 18, in the Table, penultimate entry, at line 8, delete "53372" in the column headed "Accession #" and replace by --98027--, and in the column headed "Deposit Date" insert --August 7, 1995-- opposite "98027".

Signed and Sealed this

First Day of October, 1996

Attest:

BRUCE LEHMAN

*Attesting Officer*  *Commissioner of Patents and Trademarks*

US005503991C1

(12) REEXAMINATION CERTIFICATE (4351st)
United States Patent
Gwynne et al.

(10) Number: US 5,503,991 C1
(45) Certificate Issued: May 15, 2001

(54) VECTORS FOR USE IN FILAMENTOUS FUNGI

(75) Inventors: David I. Gwynne, Brampton; Francis P. Buxton, Toronto; Mark H. Pickett, Brampton; Roger W. Davies, Ontario, all of (CA); Claudio Scazzocchio, Bures sur Yvette (FR)

(73) Assignee: Gist-Brocades N.V., Delft (NL)

Reexamination Request:
No. 90/005,095, Aug. 31, 1998

Reexamination Certificate for:
Patent No.: 5,503,991
Issued: Apr. 2, 1996
Appl. No.: 08/237,405
Filed: May 2, 1994

Certificate of Correction issued Jan. 10, 1996.

Related U.S. Application Data

(63) Continuation of application No. 07/977,832, filed on Nov. 17, 1992, now abandoned, which is a continuation of application No. 06/811,404, filed on Dec. 20, 1985, now Pat. No. 5,198,345.

(30) Foreign Application Priority Data

Apr. 15, 1985 (CA) ......................................... 479135

(51) Int. Cl.[7] ............................ C12N 15/63; C12N 15/80
(52) U.S. Cl. .................. 435/69.1; 435/252.3; 435/254.1; 435/254.11; 435/254.3; 435/256.1; 435/320.1; 536/23.1; 536/24.1
(58) Field of Search ............................... 435/69.1, 320.1, 435/471, 476, 484, 252.3, 254.1, 254.11, 254.3; 536/23.1, 23.74, 24.1

(56) References Cited

U.S. PATENT DOCUMENTS

| 4,816,405 | 3/1989 | Yelton et al. | 435/252.33 |
| 4,885,249 | 12/1989 | Buxton et al. | 435/6 |
| 5,364,770 | 11/1994 | Berka et al. | 435/69.1 |

FOREIGN PATENT DOCUMENTS

WO8402921  8/1984  (WO) .

OTHER PUBLICATIONS

"Recombinant DNA: A Short Course" by James D. Watson, John Tooze and David T. Kurtz, pp. 72–90, Scientific American Books, W. H. Freeman and Co., New York, 1983.*

"Allelix Introduces Systems for Engineered Expression of Proteins by Filamentous Fungi", Press Release by Allelix, Inc., Dec. 11, 1985.

E. Boel, M.T. Hansen, L. Hjort, L. Hoegh and N.P. Fiil, "Two Different Types of Intervening Sequences in the Glucoamylase Gene from *Aspergillus niger*", *Chemical Abstracts*, vol. 101, p. 158, abstract No. 145009y.

E. Boel, M.T. Hansen, L. Hjort, L. Hoegh and N.P. Fiil, "Two Different Types of Intervening Sequences in the Glucoamylase Gene from *Aspergillus niger*" *EMBO Journal*, vol. 3, No. 7, 1581–1585 (1984).

R.W. Davies, C. Scazzocchio, "Investigation on the Molecular Basis of the Control of Gene Expression in *A. nidulans*", Medical Research Council (MRC) Application for a Project Grant, submitted Apr. 4, 1978.

T. Goosen, L.M.J. Wennekes, K. Wernars, C.A.M.J.J. van den Hondel, H.W.J. van den Broek, "Biochemical analysis of *A. nidulans* amdS transformants", *Proceedings of the EMBO Workshop: Gene Expression in Filamentous Fungi*, meeting held Apr. 17–19, 1984 at Rhenen, The Netherlands.

M.A. John and J.F. Peberdy, "Transformation of *Aspergillus nidulans* using the argB gene", *Enzyme Microb. Technol.*, vol. 6, 386–389 (1984).

I.L. Johnstone entitled "Integrative Transformation of *A. nidulans* Using the *A. nidulans* OTCase Gene as a Selectable Marker", *Proceedings of the EMBO Workshop: Gene Expression in Filamentous Fungi*, meeting held Apr. 17–19, 1984 at Rhenen, The Netherlands.

J.M. Kelly and M.J. Hynes, "Transformation of *Aspergillus Niger* by the amdS Gene of *Aspergillus nidulans*," *The EMBO Journal*, vol. 4 No. 2, 475–479 (Feb. 1985).

Kos, J. Kuijvenhoven, P.H. Pouwels, H.W.J. van den Broek and C.A.M.J.J. van den Hondel, "Construction of a Cloning Vector for *Aspergillus niger*", *Proceedings of the EMBO Workshop: Gene Expression in Filamentous Fungi*, meeting held Apr. 17–19, 1984 at Rhenen, The Netherlands.

R.A. Lockington, "Molecular Investigations of the Ribosomal RNA Genes and the Ethanol Utilisation Genes of *Aspergillus nidulans*", Thesis, submitted to the University of Essex for the Degree of Doctor of Philosophy, Oct. 1984.

R.A. Lockington, "The Cloning of Ethanol and Threonine Inducible Genes in *Aspergillus nidulans*", *Proceedings of the EMBO Workshop: Gene Expression in Filamentous Fungi*, meeting held Apr. 17–19, 1984 at Rhenen, The Netherlands.

R.A. Lockington, H.M. Sealy–Lewis, C. Scazzocchio, and R. Wayne Davies, "Cloning and Characterization of the Ethanol Utilization Regulon in *Aspergillus nidulans*", *Gene*, vol. 33, 137–149 (1985).

(List continued on next page.)

*Primary Examiner*—David Guzo

(57) ABSTRACT

Novel vectors are disclosed for use in filamentous fungi such as Aspergillus sp. in particular, whereby protein coding regions may be inserted therein to achieve expression or expression followed by secretion of the coded protein from the host. Signal peptide sequences and promoter sequences valuable for this purpose are disclosed as are expression vectors containing coding regions native or foreign to the fungal host. In accordance with the invention, a filamentous fungus such as Aspergillus may be provided with foreign or natural coding regions associated with foreign or natural promoter sequences and optionally signal peptide sequences which can be used to control the expression and/or secretion of the proteins encoded by these coding regions.

OTHER PUBLICATIONS

J.H. Nunberg, J.H. Meade, G. Cole, F.C. Lawyer, P. McCabe, V. Schweickart, R. Tal, V.P. Wittman, J.E. Flatgaard and M.A. Innis, "Molecular Cloning and Characterization of the Glucoamylase Gene of *Aspergillus awamori*", *Molecular and Cellular Biology*, vol. 4 No. 11, 2306–2315 (Nov. 1984).

C. Scazzocchio, "Transformation in *Aspergillus nidulans*", Science Research Council (SRC) Application for a Project Grant, submitted Sep. 3, 1981.

C. Scazzocchio, "Transformation of *Aspergillus nidulans*", Science Research Council (SRC) Application for a Project Grant, submitted Apr. 29, 1983.

C. Scazzocchio, R.W. Davies, "Investigation on the Molecular Basis of the Control of Gene Expression in *A. nidulans*", Medical Research Council (MRC) Application for a Project Grant, submitted Feb. 4, 1982.

C. Scazzocchio, H.M. Sealy–Lewis, "Cloning of Two Inter-–Related Alcohol Dehydrogenases in *Aspergillus nidulans*", Science Research Council (SRC) Application for a Project Grant, submitted Mar. 26, 1982.

J. Tilburn, C. Scazzocchio, G.G. Taylor, J.H. Zabicky–Zissman, R.A. Lockington and R. Wayne Davies, "Transformation by integration in *Aspergillus nidulans*" *Gene*, vol. 26, 205–221 (1983).

J. Tilburn and C. Scazzocchio, "Analysis of Integration Events in Transformants Obtained by Transformation of *Aspergillus nidulans* With Plasmids Carrying the Acetamidase Structural Gene", *Proceedings of the EMBO Workshop: Gene Expression in Filamentous Fungi*, meeting held Apr. 17–19, 1984 at Rhenen, The Netherlands.

W.E. Timberlake, "Development of Molecular Cloning Vectors for Investigating Fungal Sporulation", USDA/SEA Competitive Grants Program, United States Department of Agriculture, Science and Education Administration, submitted Jan. 21, 1982.

G. Turner, M. Ward and C.M. Lazarus, "Cloning of the oliC$^r$ Locus of *Aspergillus nidulans* Coding for the Mitochondrial ATP Synthetase Dicyclohexycarbodiimide–Binding Protein, and Transformation of a Sensitive Strain to Oligomycin Resistance", *Proceedings of the EMBO Workshop: Gene Expression in Filamentous Fungi*, meeting held Apr. 17–19, 1984 at Rhenen, The Netherlands.

C.A.M.J.J. van den Hondel, R.F.M. van Gorcom, T. Goosen, H.W.J. van den Broek, W.E. Timberlake, P.H. Pouwels, "Development of a System for Analysis of Regulation Signals in Aspergillus", Journal of Cellular Biochemistry, 14$^{th}$ Annual Meeting Abstracts, UCLA Symposia on Molecular & Cellular Biology held Apr. 6–Apr. 25, 1985, Supplement 9C, 168, abstract No. 1557, (1985).

C.A.M.J.J. van den Hondel, R.F.M. van Gorcom, T. Goosen, H.W.J. van den Broek, W.E. Timberlake, P.H. Pouwels, "Development of a System for Analysis of Regulation Signals in Aspergillus", *Chemical Abstracts*, vol. 104, No. 13, p. 167, abstract No. 103393a (1986).

R.F.M. van Gorcom, P.J. Punt, K. Wernars, P.H. Pouwels and C.A.M.J.J. van den Hondel, "Isolation of Autonomously Replicating Sequences of *Aspergillus nidulans*" *Proceedings of the EMBO Workshop: Gene Expression in Filamentous Fungi*, meeeting held Apr. 17–19, 1984 at Rhenen, The Netherlands.

R.F.M. van Gorcom, P.H. Pouwels, T. Goosen, J. Visser, H.W.J. van den Broek, J.E. Hamer, W.E. Timberlake, and C.A.M.J.J. van den Hondel, "Expression of an *Escherichia coli* β–galactosidase fusion . . . ", *Gene*, vol. 40, 99–106 (1985).

R.F.M. van Gorcom, J.A.M. Krose, J. Visser, T. Goosen, W.E. Timberlake, P.H. Pouwels and C.A.M.J.J. Van Den Hondel, "Construction of a System for the Cloning and Analysis of Promoters in Aspergillus: Expression of the *E. coli* –galactosidase gene in *Aspergillus nidulans*", *Proceedings of the EMBO Workshop: Gene Expression in Filamentous Fungi*, meeting held Apr. 17–19, 1984, at Rhenen, The Netherlands. (abstract).

R.F.M. van Gorcom, J.A.M. Krose, J. Visser, T. Goosen, W.E. Timberlake, P.H. Pouwels and C.A.M.J.J. Van Den Hondel, "Construction of a System for the Cloning and Analysis of Promoters in Aspergillus: Expression of the *E. coli* β–galactosidase gene in *Aspergillus nidulans*", *Proceedings of the EMBO Workshop: Gene Expression in Filamentous Fungi*, meeting held Apr. 17–19, 1984, at Rhenen, The Netherlands. (poster).

R.F.M. van Gorcom, J.A.M. Krose, P.H. Pouwels, C.A.M.J.J. van den Hondel, K. Wernars, T. Goosen, J. Visser, H.W.J. van den Broek and W.E. Timberlake, "Development of a System for the Isolation and Analysis of Promoters from Aspergillus: Expression of the *E. coli* β–galactosidase gene in *A. nidulans*," Third European Congress on Biotechnology, vol. III, 305–10 (Sep. 1984).

K. Wernars, T. Goosen, R.F.M. van Gorcom, H.W.J. van den Broek and C.J. Bos, "Transformation of *A. nidulans* using Conidial Protoplasts", *Proceedings of the EMBO Workshop: Gene Expression in Filamentous Fungi*, meeeting held Apr. 17–19, 1984 at Rhenen, The Netherlands.

M.M. Yelton, J.E. Hamer, and W.E. Timberlake, "Transformation of *Aspergillus nidulans* by using a trpC plasmid", *Proc. Natl. Acad. Sci. USA*, vol. 81, 1470–1474 (1984).

* cited by examiner

US 5,503,991 C1

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1 and 9 are cancelled.

Claims 2–6, 10–12 and 14 are determined to be patentable as amended.

Claims 7, 8, 13 and 15–18, dependent on an amended claim, are determined to be patentable.

New claims 19 and 20 are added and determined to be patentable.

2. A DNA construct according to claim [1] *19*, wherein said Aspergillus host is *Aspergillus niger*.

3. A DNA construct according to claim [1] *19*, wherein said Aspergillus host is *Aspergillus nidulans*.

4. A DNA construct according to claim [1] *19*, wherein said promoter DNA comprises the alcA promoter native to *Aspergillus nidulans* operably linked to the *C. fimi* endoglucanase coding region.

5. A DNA construct according to claim 1 wherein the [coding] DNA *coding for the produced polypeptide is entirely* foreign to said Aspergillus host.

6. A DNA construct according to claim [1] *19*, further comprising a DNA fragment encoding a promoter-inducer substance.

10. A strain according to claim [9] *20*, wherein said strain is a transformed Aspergillus species selected from the group consisting of *Aspergillus nidulans* and *Aspergillus niger*.

11. A strain according to claim [9] *20*, wherein the coding DNA is foreign to said Aspergillus strain.

12. A strain according to claim [9] *20*, wherein said promoter DNA comprises alcA promoter native to *Aspergillus nidulans*.

14. A method for producing a polypeptide, said method comprising the steps of culturing an Aspergillus strain transformed by a DNA construct in which DNA coding for [a] *the produced* polypeptide is linked operably to promoter DNA for promoting transcription in Aspergillus, said DNA coding for said *produced* polypeptide being *entirely* foreign to said promoter DNA, *and isolating and purifying the produced polypeptide*.

*19. A DNA construct for use in transforming an Aspergillus host to obtain expression therein of a polypeptide, said DNA construct comprising promoter DNA for promoting transcription in Aspergillus and operably linked to DNA coding for said polypeptide to enable expression thereof in said Aspergillus host, said DNA coding for said polypeptide comprising DNA coding for a produced polypeptide, the DNA coding for the produced polypeptide being entirely foreign to said promoter DNA.*

*20. An Aspergillus strain which upon culturing expresses a polypeptide as a result of having been transformed by a DNA construct in which DNA coding for the polypeptide is linked operably to promoter DNA for promoting transcription in Aspergillus, said DNA coding for said polypeptide comprising DNA coding for a produced polypeptide, the DNA coding for the produced polypeptide being entirely foreign to said promoter DNA.*

* * * * *